US010053683B2

(12) United States Patent
Pasqual et al.

(10) Patent No.: US 10,053,683 B2
(45) Date of Patent: Aug. 21, 2018

(54) INTERCELLULAR LABELING OF LIGAND-RECEPTOR INTERACTIONS

(71) Applicant: Whitehead Institute for Biomedical Research, Cambridge, MA (US)

(72) Inventors: Giulia Pasqual, Somerville, MA (US); Gabriel Victora, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 20 days.

(21) Appl. No.: 14/875,140

(22) Filed: Oct. 5, 2015

(65) Prior Publication Data

US 2016/0097773 A1    Apr. 7, 2016

Related U.S. Application Data

(60) Provisional application No. 62/059,452, filed on Oct. 3, 2014.

(51) Int. Cl.
| | |
|---|---|
| *G01N 33/53* | (2006.01) |
| *C12N 9/52* | (2006.01) |
| *A01K 67/027* | (2006.01) |
| *G01N 33/50* | (2006.01) |

(52) U.S. Cl.
CPC .............. *C12N 9/52* (2013.01); *A01K 67/027* (2013.01); *A01K 67/0275* (2013.01); *G01N 33/5008* (2013.01); *G01N 33/5047* (2013.01); *A01K 2217/072* (2013.01); *A01K 2227/105* (2013.01); *A01K 2267/03* (2013.01); *A01K 2267/0387* (2013.01); *C07K 2319/70* (2013.01); *C12Y 304/2207* (2013.01); *G01N 2333/70532* (2013.01); *G01N 2333/70578* (2013.01)

(58) Field of Classification Search
None
See application file for complete search history.

(56) References Cited

U.S. PATENT DOCUMENTS

| | | | |
|---|---|---|---|
| 5,728,369 | A | 3/1998 | Griffiths et al. |
| 8,211,656 | B2 | 7/2012 | Hyde et al. |
| 8,940,501 | B2 | 1/2015 | Ploegh et al. |
| 2003/0022178 | A1 | 1/2003 | Schneewind et al. |
| 2003/0224490 | A1 | 12/2003 | Dessain et al. |
| 2004/0213795 | A1 | 10/2004 | Collins et al. |
| 2011/0195068 | A1 | 8/2011 | Langermann et al. |
| 2011/0321183 | A1 | 12/2011 | Ploegh et al. |
| 2012/0039906 | A1 | 2/2012 | Olive |
| 2012/0114649 | A1 | 5/2012 | Langermann et al. |
| 2013/0095098 | A1 | 4/2013 | Tyson |
| 2013/0108651 | A1 | 5/2013 | Carven et al. |
| 2013/0109843 | A1 | 5/2013 | Carven et al. |
| 2013/0237580 | A1 | 9/2013 | Sasikumar et al. |
| 2014/0030697 | A1 | 1/2014 | Ploegh et al. |
| 2014/0057317 | A1 | 2/2014 | Liu et al. |
| 2014/0249296 | A1 | 9/2014 | Ploegh et al. |
| 2016/0082046 | A1 | 3/2016 | Lodish et al. |
| 2016/0122707 | A1* | 5/2016 | Swee ................. A61K 39/0011 424/93.7 |
| 2016/0287734 | A1 | 10/2016 | Rashidian et al. |

FOREIGN PATENT DOCUMENTS

| | | |
|---|---|---|
| JP | 2010115136 A | 5/2010 |
| WO | WO 2000/62804 A2 | 10/2000 |
| WO | WO 2005/051976 A2 | 6/2005 |
| WO | WO 2010/087994 A2 | 8/2010 |
| WO | WO 2011/133704 A2 | 10/2011 |
| WO | WO 2012/142659 A1 | 10/2012 |
| WO | WO 2013/003555 A1 | 1/2013 |

OTHER PUBLICATIONS

Park et al (Chem. Commun., 2013, vol. 49, pp. 9585-9587).*
Extended European Search Report, dated Nov. 30, 2012, in connection with EP 10736161.0.
Invitation to Pay Additional Fees, dated Nov. 8, 2010, in connection with PCT/US2010/000274.
International Search Report and Written Opinion, dated Dec. 22, 2010, in connection with PCT/US2010/000274.
International Preliminary Report on Patentability, dated Aug. 11, 2011, in connection with PCT/US2010/000274.
Extended European Search Report, dated Nov. 26, 2014, in connection with EP 12804570.5.
International Search Report and Written Opinion, dated Nov. 15, 2012, in connection with PCT/US2012/044584.
International Preliminary Report on Patentability, dated Jan. 16, 2014, in connection with PCT/US2012/044584.
Invitation to Pay Additional Fees, dated Sep. 5, 2014, in connection with PCT/US2014/037554.
International Search Report and Written Opinion, dated Nov. 6, 2014, in connection with PCT/US2014/037554.
International Preliminary Report on Patentability, dated Nov. 19, 2015, in connection with PCT/US2014/037554.
International Search Report and Written Opinion, dated Oct. 27, 2014, in connection with PCT/US2014/037545.
International Preliminary Report on Patentability, dated Nov. 19, 2015, in connection with PCT/US2014/037545.
Invitation to Pay Additional Fees, dated Mar. 20, 2015, in connection with PCT/US14/65574.
International Search Report and Written Opinion, dated Jun. 4, 2015, in connection with PCT/US14/65574.
Antos et al., A straight path to circular proteins. J Biol Chem. Jun. 5, 2009;284(23):16028-36. Epub Apr. 9, 2009.
Antos et al., Lipid modification of proteins through sortase-catalyzed transpeptidation. J Am Chem Soc. Dec. 3, 2008;130(48):16338-43.

(Continued)

*Primary Examiner* — Celine Qian
(74) *Attorney, Agent, or Firm* — Wolf, Greenfield & Sacks, P.C.

(57) ABSTRACT

An sortase-mediated intercellular labeling method allowing for tracking ligand-receptor interaction both in vitro and in vivo; and uses thereof for tracking molecule interactions both in vitro and in vivo, identifying modulators of ligand-receptor interaction, identifying potential binding partners of a protein of interest, identifying B cells expressing high affinity B cell receptors to antigens, and identifying the antigen to which a T cell of interest binds.

31 Claims, 11 Drawing Sheets

(56) References Cited

OTHER PUBLICATIONS

Antos et al., Site-specific N- and C-terminal labeling of a single polypeptide using sortases of different specificity. J Am Chem Soc. Aug. 12, 2009;131(31):10800-1. doi: 10.1021/ja902681k.

Barnett et al., Differential recognition of surface proteins in *Streptococcus pyogenes* by two sortase gene homologs. J Bacteriol. Apr. 2002;184(8):2181-91.

Boonyarattanakalin et al., Synthesis of an artificial cell surface receptor that enables oligohistidine affinity tags to func-tion as metal-dependent cell-penetrating peptides. J Am Chem Soc. Mar. 18, 2006;128(14):4917.

Chan et al., Covalent attachment of proteins to solid supports and surfaces via Sortase-mediated ligation. PLoS One. Nov. 14, 2007;2(11):e1164. 5 pages.

Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.

Clow et al., Immobilization of proteins to biacore sensor chips using *Staphylococcus aureus* sortase A. Biotechnol Lett. Sep. 2008;30(9):1603-7. Epub Apr. 15, 2008.

Dorr et al., Reprogramming the specificity of sortase enzymes. Proc Natl Acad Sci U S A. Sep. 16, 2014;111(37):13343-8. doi:10.1073/pnas.1411179111. Epub Sep. 3, 2014.

Kruger et al., Analysis of the substrate specificity of the *Staphylococcus aureus* sortase transpeptidase SrtA. Biochemistry. Feb. 17, 2004;43(6):1541-51.

Levary et al., Protein-protein fusion catalyzed by sortase A. PLoS One. Apr. 6, 2011;6(4):e18342. doi: 10.1371/journal.pone.0018342. 6 pages.

Mao et al., Sortase-Mediated Protein Ligation: A New Method for Portein Engineering. J Am Chem Soc. Feb. 10, 2004;126:2670-1.

Mao, A self-cleavable sortase fusion for one-step purification of free recombinant proteins. Protein Expr Purif. Sep. 2004;37(1):253-63.

Maresso et al., Surface protein IsdC and Sortase B are required for heme-iron scavenging of Bacillus anthracis. J Bacteriol. Dec. 2006;188(23):8145-52. Epub Sep. 29, 2006.

Mariscotti et al., The Listeria monocytogenes sortase-B recognizes varied amino acids at position 2 of the sorting motif. J Biol Chem. Mar. 6, 2009;284(10):6140-6. Epub Jan. 7, 2009.

Marraffini et al., Sortase C-mediated anchoring of BasI to the cell wall envelope of Bacillus anthracis. J Bacteriol. Sep. 2007;189(17):6425-36. Epub Jun. 22, 2007.

Matsumoto et al., Site-specific tetrameric streptavidin-protein conjugation using sortase A. J Biotechnol. Mar. 10, 2011;152(1-2):37-42. doi: 10.1016/j.jbiotec.2011.01.008. Epub Jan. 22, 2011.

Mazmanian et al., An iron-regulated sortase anchors a class of surface protein during *Staphylococcus aureus* pathogenesis. Proc Natl Acad Sci U S A. Feb. 19, 2002;99(4):2293-8. Epub Feb. 5, 2002.

Mazmanian et al., Sortase-catalysed anchoring of surface proteins to the cell wall of *Staphylococcus aureus*. Mol Microbiol. Jun. 2001;40(5):1049-57. Review.

Namavari et al., A novel method for direct site-specific radiolabeling of peptides using [18F]FDG. Bioconjug Chem. Mar. 18, 2009;20(3):432-6. doi: 10.1021/bc800422b.

Ning et al., Visualizing metabolically labeled glycoconjugates of living cells by copper-free and fast huisgen cycloadditions. Angew Chem Int Ed Engl. 2008;47(12):2253-5.

Pallen et al., An embarrassment of sortases—a richness of substrates? Trends Microbiol. Mar. 2001;9(3):97-101.

Parthasarathy et al., Sortase A as a novel molecular "stapler" for sequence-specific protein conjugation. Bioconjug Chem. Mar.-Apr. 2007;18(2):469-76. Epub Feb. 16, 2007.

Paterson et al., Enzyme-mediated site-specific bioconjugation of metal complexes to proteins: sortase-mediated coupling of copper-64 to a single-chain antibody. Angew Chem Int Ed Engl. Jun. 10, 2014;53(24):6115-9. doi: 10.1002/anie.201402613. Epub Apr. 28, 2014.

Pellois et al., A ligation and photorelease strategy for the temporal and spatial control of protein function in living cells. Angew Chem Int Ed Engl. Sep. 5, 2005;44(35):5713-7.

Piotukh et al., D. Directed evolution of sortase A mutants with altered substrate selectivity profiles. J Am Chem Soc. Nov. 9, 2011;133(44):17536-9. doi: 10.1021/ja205630g. Epub Oct. 13, 2011.

Popp et al., Making and breaking peptide bonds: protein engineering using sortase. Angew Chem Int Ed Engl. May 23, 2011;50(22):5024-32. doi:10.1002/anie.201008267. Epub Apr. 27, 2011.

Popp et al., Site-specific protein labeling via sortase-mediated transpeptidation. Curr Protoc Protein Sci. Apr. 2009;Chapter 15:Unit 15.3. doi: 10.1002/0471140864.ps1503s56.

Popp et al., Sortagging: a versatile method for protein labeling. Nat Chem Biol. Nov. 2007;3(11):707-8. Epub Sep. 23, 2007.

Popp et al., Sortase-catalyzed transformations that improve the properties of cytokines. Proc Natl Acad Sci USA. Feb. 22, 2011;108(8):3169-74. doi: 10.1073/pnas.1016863108. Epub Feb. 4, 2011.

Popp et al., Substrate filtering by the active site crossover loop in UCHL3 revealed by sortagging and gain-of-function mutations. J Biol Chem. Feb. 6, 2009;284(6):3593-602. Epub Dec. 1, 2008.

Race et al., Crystal structure of *Streptococcus pyogenes* sortase A: implications for sortase mechanism. J Biol Chem. Mar. 13, 2009;284(11):6924-33. Epub Jan. 6, 2009.

Samantaray et al., Peptide-sugar ligation catalyzed by transpeptidase sortase: a facile approach to neoglycoconjugate synthesis. J Am Chem Soc. Feb. 20, 2008;130(7):2132-3. Epub Jan. 30, 2008.

Strijbis et al., Protein ligation in living cells using sortase. Traffic. Jun. 2012;13(6):780-9. doi: 10.1111/j.1600-0854.2012.01345.x. Epub Mar. 23, 2012.

Swee et al., Sortase-mediated modification of αDEC205 affords optimization of antigen presentation and immunization against a set of viral epitopes. Proc Natl Acad Sci USA. Jan. 22, 2013;110(4):1428-33. doi: 10.1073/pnas.1214994110. Epub Jan. 7, 2013.

Tanaka et al., Site-specific protein modification on living cells catalyzed by Sortase. Chembiochem. Mar. 25, 2008;9(5):802-7.

Theile et al., Site-specific N-terminal labeling of proteins using sortase-mediated reactions. Nat Protoc. Sep. 2013;8(9):1800-7. doi: 10.1038/nprot.2013.102. Epub Aug. 29, 2013.

Ton-That et al., Anchoring of surface proteins to the cell wall of *Staphylococcus aureus*. Sortase catalyzed in vitro transpeptidation reaction using LPXTG peptide and NH(2)-Gly(3) substrates. J Biol Chem. Mar. 31, 2000;275(13):9876-81.

Ton-That et al., Protein sorting to the cell wall envelope of Gram-positive bacteria. Biochim Biophys Acta. Nov. 11, 2004;1694(1-3):269-78.

Ton-That et al., Purification and characterization of sortase, the transpeptidase that cleaves surface proteins of *Staphylococcus aureus* at the LPXTG motif. Proc Natl Acad Sci U S A. Oct. 26, 1999;96(22):12424-9.

Witte et al., Preparation of unnatural N-to-N and C-to-C protein fusions. Proc Natl Acad Sci U S A. Jul. 24, 2012;109(30):11993-8. doi: 10.1073/pnas.1205427109. Epub Jul. 9, 2012.

Witte et al., Production of unnaturally linked chimeric proteins using a combination of sortase-catalyzed transpeptidation and click chemistry. Nat Protoc. Sep. 2013;8(9):1808-19. doi: 10.1038/nprot.2013.103. Epub Apr. 4, 2014. 16 pages.

Wu et al., Sortase A-catalyzed transpeptidation of glycosylphosphatidylinositol derivatives for chemoenzymatic synthesis of GPI-anchored proteins. J Am Chem Soc. Feb. 10, 2010;132(5):1567-71. doi: 10.1021/ja906611x.

Yamamoto et al., Expansion of the sortase-mediated labeling method for site-specific N-terminal labeling of cell surface proteins on living cells. Chem Commun (Camb). Mar. 7, 2009;(9):1022-4. doi: 10.1039/b818792d. Epub Jan. 7, 2009.

GenPept Accession No. YP 187332.1. Gill et al. Dec. 17, 2014.

Ahlgren et al., Targeting of HER2-expressing tumors with a site-specifically 99mTc-labeled recombinant affibody molecule,

(56) References Cited

OTHER PUBLICATIONS

ZHER2:2395, with C-terminally engineered cysteine. J Nucl Med. May 2009;50(5):781-9. doi: 10.2967/jnumed.108.056929. Epub Apr. 16, 2009.

Chang et al., Development and characterization of 89Zr-labeled panitumumab for immuno-positron emission tomographic imaging of the epidermal growth factor receptor. Mol Imaging. Jan.-Feb. 2013;12(1):17-27.

De Meyer et al., Nanobody-based products as research and diagnostic tools. Trends Biotechnol. May 2014;32(5):263-70. doi:10.1016/j.tibtech.2014.03.001. Epub Apr. 1, 2014.

Delgado, et al. "Stabilities of divalent and trivalent metal ion complexes of macrocyclic triazatriacetic acids.", Inorg. Chem. 1999; 32, 3320-3326.

Dijkers et al., Biodistribution of 89Zr-trastuzumab and PET imaging of HER2-positive lesions in patients with metastatic breast cancer. Clin Pharmacol Ther. May 2010;87(5):586-92. doi:10.1038/clpt.2010.12. Epub Mar. 31, 2010.

Engfeldt et al., Chemical synthesis of triple-labelled three-helix bundle binding proteins for specific fluorescent detection of unlabelled protein. Chembiochem. Jun. 2005;6(6):1043-50.

Goldenberg et al., Novel radiolabeled antibody conjugates. Oncogene. May 28, 2007;26(25):3734-44.

Groheux et al., Correlation of high 18F-FDG uptake to clinical, pathological and biological prognostic factors in breast cancer. Eur J Nucl Med Mol Imaging. Mar. 2011;38(3):426-35. doi:10.1007/s00259-010-1640-9. Epub Nov. 6, 2010.

Hochuli et al., Genetic Approach to Facilitate Purification of Recombinant Proteins with a Novel Metal Chelate Adsorbent. Nature Biotechnology. 1988, 6, 1321-1325.

Holm et al., Electrophilic affibodies forming covalent bonds to protein targets. J Biol Chem. Nov. 20, 2009;284(47):32906-13. doi:10.1074/jbc.M109.034322. Epub Sep. 15, 2009.

Keliher et al., High-yielding, two-step 18F labeling strategy for 18F-PARP1 inhibitors. ChemMedChem. Mar. 7, 2011;6(3):424-7. doi: 10.1002/cmdc.201000426. Epub Jan. 4, 2011.

Knowles et al., Advances in immuno-positron emission tomography: antibodies for molecular imaging in oncology. J Clin Oncol. Nov. 1, 2012;30(31):3884-92. doi: 10.1200/JCO.2012.42.4887. Epub Sep. 17, 2012.

Langenhan et al., "Recent Carbohydrate-Based Chemoselective Ligation Applications." Current Organic Synthesis. 2005; 2, 59-81.

Lundberg et al., Site-specifically conjugated anti-HER2 Affibody molecules as one-step reagents for target expression analyses on cells and xenograft samples. J Immunol Methods. Jan. 30, 2007;319(1-2):53-63. Epub Nov. 21, 2006.

Nair-Gill et al., Non-invasive imaging of adaptive immunity using positron emission tomography. Immunol Rev. Feb. 2008;221:214-28. doi: 10.1111/j.1600-065X.2008.00585.x.

Nayak et al., PET and MRI of metastatic peritoneal and pulmonary colorectal cancer in mice with human epidermal growth factor receptor 1-targeted 89Zr-labeled panitumumab. J Nucl Med. Jan. 2012;53(1):113-20. doi: 10.2967/jnumed.111.094169.

Orlova et al., Evaluation of [(111/114m)In]CHX-A"-DTPA-ZHER2:342, an affibody ligand coniugate for targeting of HER2-expressing malignant tumors. Q J Nucl Med Mol Imaging. 2007.

Orlova et al., Tumor imaging using a picomolar affinity HER2 binding affibody molecule. Cancer Res. Apr. 15, 2006;66(8):4339-48.

Poli et al., Radretumab radioimmunotherapy in patients with brain metastasis: a 124I-L19SIP dosimetric PET study. Cancer Immunol Res. Aug. 2013;1(2):134-43. doi: 10.1158/2326-6066.CIR-13-0007. Epub May 20, 2013.

Rashidian et al., A highly efficient catalyst for oxime ligation and hydrazone-oxime exchange suitable for bioconjugation. Bioconjug Chem. Mar. 20, 2013;24(3):333-42. doi: 10.1021/bc3004167. Epub Mar. 6, 2013.

Rashidian et al., Enzymatic labeling of proteins: techniques and approaches. Bioconjug Chem. Aug. 21, 2013;24(8):1277-94.

Salsano et al., "PET imaging using radiolabeled antibodies: future direction in tumor diagnosis and correlate applications." Research and Reports in Nuclear Medicine. 2013: 3; 9-17.

Siontorou, Nanobodies as novel agents for disease diagnosis and therapy. Int J Nanomedicine. 2013;8:4215-27. doi: 10.2147/IJN.S39428. Epub Jan. 11, 2013.

Spicer et al., Selective chemical protein modification. Nat Commun. Sep. 5, 2014;5:4740. doi: 10.1038/ncomms5740.

Tanaka et al., PET (positron emission tomography) imaging of biomolecules using metal—DOTA complexes: a new collaborative challenge by chemists, biologists, and physicians for future diagnostics and exploration of in vivo dynamics. Org Biomol Chem. Mar. 7, 2008;6(5):815-28. doi: 10.1039/b718157b. Epub Feb. 1, 2008.

Tolmachev et al., Radionuclide therapy of HER2-positive microxenografts using a 177Lu-labeled HER2-specific Affibody molecule. Cancer Res. Mar. 15, 2007;67(6):2773-82.

Tran et al., (99m)Tc-maEEE-Z(HER2:342), an Affibody molecule-based tracer for the detection of HER2 expression in malignant tumors. Bioconjug Chem. Nov.-Dec. 2007;18(6):1956-64. Epub Oct. 19, 2007.

Truong et al., Copper-catalyzed, directing group-assisted fluorination of arene and heteroarene C—H bonds. J Am Chem Soc. Jun. 26, 2013;135(25):9342-5. doi: 10.1021/ja4047125. Epub Jun. 12, 2013.

Vaidyanathan et al., Synthesis of N-succinimidyl 4-[18F]fluorobenzoate, an agent for labeling proteins and peptides with 18F. Nat Protoc. 2006;1(4):1655-61.

Vosjan et al., Conjugation and radiolabeling of monoclonal antibodies with zirconium-89 for PET imaging using the bifunctional chelate p-isothiocyanatobenzyl-desferrioxamine. Nat Protoc. Apr. 2010;5(4):739-43. doi: 10.1038/nprot.2010.13. Epub Mar. 25, 2010.

Waldherr et al., Monitoring antiproliferative responses to kinase inhibitor therapy in mice with 3'-deoxy-3'-18F-fluorothymidine PET. J Nucl Med. Jan. 2005;46(1):114-20.

Youssef et al., The use of 18F-FDG PET in the diagnosis of cardiac sarcoidosis: a systematic review and metaanalysis including the Ontario experience. J Nucl Med. Feb. 2012;53(2):241-8. doi: 10.2967/jnumed.111.090662. Epub Jan. 6, 2012.

Zhang et al., Positron emission tomography imaging of CD105 expression with a 64Cu-labeled monoclonal antibody: NOTA is superior to DOTA. PLoS One. 2011;6(12):e28005. doi:10.1371/journal.pone.0028005. Epub Dec. 9, 2011.

Zong et al., Crystal structures of *Staphylococcus aureus* sortase A and its substrate complex. J Biol Chem. Jul. 23, 2004;279(30):31383-9. Epub Apr. 26, 2004.

Extended European Search Report, dated Nov. 9, 2016, in connection with EP 14795167.7.

Extended European Search Report, dated Oct. 13, 2016, in connection with EP 14795120.6.

Hackenberger et al., Chemoselective ligation and modification strategies for peptides and proteins. Angew Chem Int Ed Engl. 2008;47(52):10030-74. doi: 10.1002/anie.200801313.

Lu et al. Biologic properties and enucleation of red blood cells from human embryonic stem cells. Blood. Dec. 1, 2008;112(12):4475-84. doi:10.1182/blood-2008-05-157198. Epub Aug. 19, 2008.

Muzykantov, Drug delivery by red blood cells: vascular carriers designed by mother nature. Expert Opin Drug Deliv. Apr. 2010;7(4):403-27. doi:10.1517/17425241003610633.

Pishesha et al., Engineered erythrocytes covalently linked to antigenic peptides can protect against autoimmune disease. Proc Natl Acad Sci U S A. Mar. 21, 2017;114(12):3157-3162. doi:10.1073/pnas.1701746114. Epub Mar. 7, 2017.

Shi et al. Engineered red blood cells as carriers for systemic delivery of a wide array of functional probes. Proc Natl Acad Sci U S A. Jul. 15, 2014;111(28):10131-6. doi: 10.1073/pnas.1409861111. Epub Jun. 30, 2014.

Swee et al., One-step enzymatic modification of the cell surface redirects cellular cytotoxicity and parasite tropism. ACS Chem Biol. Feb. 20, 2015;10(2):460-5. doi: 10.1021/cb500462t.

Ta et al., Enzymatic single-chain antibody tagging: a universal approach to targeted molecular imaging and cell homing in cardiovascular disease. Circ Res. Aug. 5, 2011;109(4):365-73. doi: 10.1161/CIRCRESAHA.111.249375.

(56) References Cited

OTHER PUBLICATIONS

Wu et al., The use of sortase-mediated ligation for the immobilisation of bacterial adhesins onto fluorescence-labelled microspheres: a novel approach to analyse bacterial adhesion to host cells. Biotechnol Lett. Nov. 2010;32(11):1713-8. doi: 10.1007/s10529-010-0349-y.
Matsumura et al., Emerging principles for the recognition of peptide antigens by MHC class 1 molecules, Sci. 1992;257:927-934.
Tsukiji et al., Sortase-mediated ligation: A Gift from Gram-Positive Bacteria to Protein Engineering, ChemBioChem 2009;10:787-798.
Wriggers et al., Control of Protein Functional Dynamics by Peptide Linkers, Prat. Function. Dynam. 2005;80:736-746.
Xiao et al., Protein N-terminal processing: substrate specificity of *Escherichia coli* and human methionine aminopeptidases. Biochemistry. Jul. 6, 2010;49(26):5588-99. doi: 10.1021/bi1005464.

\* cited by examiner

SEQUENCE LISTING

<160> NUMBER OF SEQ ID NOS: 60

<210> SEQ ID NO 1
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occuring amino acid

<400> SEQUENCE: 1

Leu Pro Xaa Thr Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 2

Leu Pro Glu Thr Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 3

Gly Gly Gly Gly Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be any naturally occuring amino acid

<400> SEQUENCE: 4

Leu Pro Thr Xaa Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 5

Leu Pro Glu Thr Gly Gly
1               5

<210> SEQ ID NO 6
<211> LENGTH: 5
<212> TYPE: PRT

```
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occuring amino acid

<400> SEQUENCE: 6

Leu Ala Xaa Thr Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occuring amino acid

<400> SEQUENCE: 7

Leu Pro Xaa Ser Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 8

Leu Pro Lys Thr Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 9

Leu Pro Ala Thr Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 10

Leu Pro Asn Thr Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
```

```
<223> OTHER INFORMATION: Xaa can be any naturally occurring amino acid

<400> SEQUENCE: 11

Leu Pro Xaa Ala Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 12

Leu Pro Asn Ala Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occuring amino acid

<400> SEQUENCE: 13

Leu Pro Xaa Thr Ala
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 14

Leu Pro Asn Thr Ala
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occuring amino acid

<400> SEQUENCE: 15

Leu Gly Xaa Thr Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 16

Leu Gly Ala Thr Gly
1               5
```

```
<210> SEQ ID NO 17
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occuring amino acid

<400> SEQUENCE: 17

Ile Pro Xaa Thr Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 18

Ile Pro Asn Thr Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 19

Ile Pro Glu Thr Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 20

Leu Ala Glu Thr Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is Gln or Lys
<220> FEATURE:
<221> NAME/KEY: misc_feature
<222> LOCATION: (4)
<223> OTHER INFORMATION: Xaa is Thr or Ser
<220> FEATURE:
<221> NAME/KEY: misc_feature
<222> LOCATION: (5)
<223> OTHER INFORMATION: Xaa is Asn, Gly, or Ser

<400> SEQUENCE: 21
```

Asn Pro Xaa Xaa Xaa
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 22

Asn Pro Gln Thr Asn
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 23

Asn Pro Lys Thr Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 24

Asn Ser Lys Thr Ala
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 25

Asn Pro Gln Thr Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 26

Asn Ala Lys Thr Asn
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 27

Asn Pro Gln Ser Ser

```
1               5
```

<210> SEQ ID NO 28
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is Glu, Ala, Ser, His

<400> SEQUENCE: 28

```
Asn Ala Xaa Thr Gly
1               5
```

<210> SEQ ID NO 29
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 29

```
Gln Val Pro Thr Gly Val
1               5
```

<210> SEQ ID NO 30
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is Gln or Lys
<220> FEATURE:
<221> NAME/KEY: misc_feature
<222> LOCATION: (5)..(5)
<223> OTHER INFORMATION: Xaa is Ala or Ser

<400> SEQUENCE: 30

```
Leu Pro Xaa Thr Xaa Thr
1               5
```

<210> SEQ ID NO 31
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occuring amino acid
<220> FEATURE:
<221> NAME/KEY: misc_feature
<222> LOCATION: (5)..(5)
<223> OTHER INFORMATION: Xaa is Ala or Ser

<400> SEQUENCE: 31

```
Leu Pro Xaa Thr Xaa
1               5
```

<210> SEQ ID NO 32
<211> LENGTH: 5
<212> TYPE: PRT
<213> ORGANISM: Artificial Sequence

```
<220> FEATURE:
<223> OTHER INFORMATION: Synthetic Polypeptide

<400> SEQUENCE: 32

Leu Pro Ser Thr Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 33

Leu Pro Ile Thr Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 34

Leu Pro Asp Thr Ala
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 35

Ser Pro Lys Thr Gly
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 36

Leu Ala Ala Thr Gly
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 37

Leu Ala His Thr Gly
1               5

<210> SEQ ID NO 38
<211> LENGTH: 5
<212> TYPE: PRT
<213> ORGANISM: Artificial Sequence
<220> FEATURE:
```

<223> OTHER INFORMATION: Synthetic Polypeptide

<400> SEQUENCE: 38

Leu Ala Ser Thr Gly
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 39

Leu Pro Leu Thr Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 40

Leu Ser Arg Thr Gly
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 41

Val Pro Asp Thr Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 42

Ile Pro Gln Thr Gly
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 43

Tyr Pro Arg Arg Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Polypeptide

```
<400> SEQUENCE: 44

Leu Pro Met Thr Gly
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 45

Leu Ala Phe Thr Gly
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 46

Leu Pro Gln Thr Ser
1               5

<210> SEQ ID NO 47
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 47

Asn Pro Gln Ser
1

<210> SEQ ID NO 48
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 48

Leu Pro Ser Thr
1

<210> SEQ ID NO 49
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 49

Asn Ser Lys Thr
1

<210> SEQ ID NO 50
<211> LENGTH: 4
<212> TYPE: PRT
<213> ORGANISM: Artificial Sequence
<220> FEATURE:
<223> OTHER INFORMATION: Synthetic Polypeptide
```

```
<400> SEQUENCE: 50

Asn Pro Gln Thr
1

<210> SEQ ID NO 51
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 51

Asn Ala Lys Thr
1

<210> SEQ ID NO 52
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 52

Leu Pro Ile Thr
1

<210> SEQ ID NO 53
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 53

Leu Ala Glu Thr
1

<210> SEQ ID NO 54
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 54

Leu Pro Glu Thr
1

<210> SEQ ID NO 55
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 55

Leu Pro Glu Thr Gly Gly Gly
1               5

<210> SEQ ID NO 56
<211> LENGTH: 73
<212> TYPE: DNA
<213> ORGANISM: Mus musculus

<400> SEQUENCE: 56
tgtttttagg tccatctagg gcagtgtgga ggcggaggag gtaccgttac gtgcagtgac      60
```

```
aaacagtacc tcc                                                          73

<210> SEQ ID NO 57
<211> LENGTH: 74
<212> TYPE: DNA
<213> ORGANISM: Mus musculus

<400> SEQUENCE: 57
aattctcagt ttttctattt tagatgctgg aggcggtggt ggtaccgtgg agacgcaagc        60
ttatttcaat ggga                                                         74

<210> SEQ ID NO 58
<211> LENGTH: 38
<212> TYPE: DNA
<213> ORGANISM: Mus musculus

<400> SEQUENCE: 58
agggcagtgt ggaggcggag gaggtaccgt tacgtgca                               38

<210> SEQ ID NO 59
<211> LENGTH: 12
<212> TYPE: PRT
<213> ORGANISM: Mus musculus

<400> SEQUENCE: 59

Gly Gln Cys Gly Gly Gly Gly Gly Thr Val Thr Cys
1               5                   10

<210> SEQ ID NO 60
<211> LENGTH: 72
<212> TYPE: DNA
<213> ORGANISM: Mus musculus

<400> SEQUENCE: 60
ttttaggtcc atctagggca gtgtggaggc ggaggaggta ccgttacgtg cagtgacaaa        60
cagtacctcc ac                                                           72
```

INTERCELLULAR LABELING OF LIGAND-RECEPTOR INTERACTIONS

CROSS-REFERENCE TO RELATED APPLICATIONS

This application claims the benefit of the filing date of U.S. Provisional Application No. 62/059,452, filed Oct. 3, 2014, the entire contents of which are incorporated by reference herein.

GOVERNMENT SUPPORT

This invention was made with government support under grant number OD012146 awarded by the National Institutes of Health. The government has certain rights in the invention.

BACKGROUND OF THE INVENTION

One of the key characteristics of the immune system is the ability to react to pathogens by generating antibodies. An effective immune response requires the production of antibodies that bind antigens with high affinity and specificity. Exposure to antigen triggers the generation and clonal selection of B cells carrying novel mutant Ig sequences with improved antigen affinity, in a phenomenon known as affinity maturation. Affinity maturation is the result of the combination of two processes: somatic hypermutation and affinity-based selection, both of which occur in anatomic structures referred to as germinal centers. Recent studies suggest that the antigen-dependent interaction between B cells at germinal centers and follicular T helper (Tfh) cells, which are the limiting factor in affinity-based selection of B cells that express high affinity antibodies. According to the proposed model, B cells that exhibit high affinity Ig molecules at the plasma membrane will capture and process more antigen for presentation on major histocompatibility complex (MHC) class II molecules. A limited number of Tfh cells then selects those B cells with the highest peptide-MHC density and directs their return to the dark zones in germinal centers, where the selected B cells undergo rapid division. By contrast, B cells that fail to interact with Tfh cells undergo apoptosis.

Despite the crucial role of the interaction between Tfh cells and B cells in affinity maturation, little is known about how these interactions lead to selection of some cells and elimination of others in an in vivo setting. This gap is due largely to the fact that there is no effective way to determine the extent to which two cells have interacted within a living animal. Interactions between different ligand-receptor pairs expressed by various subsets of immune cells are key events in the immune response, but the tracking of these interactions in the context of a living animal has never been achieved.

SUMMARY OF THE INVENTION

In one aspect, the present disclosure provides an intercellular labeling method, which comprises (i) providing a first cell expressing a first polypeptide on its surface, the first polypeptide comprising a sortase acceptor peptide (e.g., GGG), which is located at the N-terminus of the first polypeptide; (ii) providing a second cell expressing a second polypeptide on its surface, the second polypeptide comprising a sortase (e.g., a sortase A, a sortase B, a sortase C, or a sortase D) or an active fragment thereof; and (iii) contacting the first cell with the second cell in the presence of a peptide comprising a sortase recognition sequence (e.g., LPTXG (SEQ ID NO: 4) for sortase A), wherein the peptide is associated with a detectable label, e.g., biotin or a fluorescent dye. In some examples, the first polypeptide may be a fusion polypeptide that comprises the sortase acceptor peptide and one member of a receptor-ligand pair. Alternatively or in addition, the second polypeptide may also be a fusion polypeptide that comprises the sortase or the active fragment thereof and the other member of the receptor-ligand pair. Exemplary receptor-ligand pairs include, but are not limited to, CD40 and CD40L, CD80 and CD28, CD80 and CTLA4, CD86 and CD28, CD86 and CTLA4, PD-1 and PD-L1, PD-1 and PD-L2, or ICOS and ICOSL. Upon interaction between the first cell and the second cell (e.g., via the receptor-ligand pair), the sortase, or the active fragment thereof links the peptide to the first polypeptide, thereby labeling the first cell expressing the first polypeptide. The first polypeptide, the second polypeptide, or both may further comprise a protein tag, which may facilitate purification and isolation of the polypeptide comprising such or cells expressing the polypeptide.

In some embodiments, the first cell, the second cell, or both are immune cells, for example, T cells, B cells, dendritic cells, macrophages, or natural killer cells. In one example, the first cell is a T cell, and the second cell is a B cell, or vice versa.

In some embodiments, the sortase used in the intercellular labeling method is a mutant sortase (e.g., a mutant sortase A) that exhibits improved catalytic activity as compared to its wild-type counterpart. In some examples, the mutant sortase A (SrtA) comprises one or more mutations of P94R or P94S, S102C, A104H, E105D, K138P, K152I, D160K or D160N, K162H, T164N, D165A, K173E, I182V, K190E, and K196S or K196T. In one example, the mutant SrtA includes mutations P94S, D160N, and K196T.

In any of the intercellular labeling methods described herein, the sortase recognition sequence is LPXTG (SEQ ID NO: 1), in which X is any amino acid residue. For example, the sortase recognition sequence is LPETG (SEQ ID NO: 2), which may be co-used with any of the sortase A enzymes, including both wild-type SrtAs and SrtA mutants disclosed herein or known in the art. Alternatively or in addition, the sortase acceptor peptide may be an oligoglycine, e.g., consisting of 1-5 glycine residues.

In some examples, the intercellular labeling method as described herein involves a first polypeptide comprising CD40 and oligoglycine GGGGG (SEQ ID NO: 3), which is located at the N-terminus of the first polypeptide, and a second polypeptide comprising CD40L, which is fused to a sortase or the active fragment thereof. The first cell may be a B cell, and the second cell may be a T cell.

The intercellular labeling method described herein may be performed in vitro. Alternatively, it may be performed in vivo. In the latter case, the first cell, the second cell, or both may be endogenous cells of a non-human transgenic animal (i.e., cells produced in the transgenic animal). Exemplary non-human transgenic animals include, but are not limited to, transgenic mouse, transgenic rat, or transgenic rabbit. In some embodiments, the first cell is an endogenous cell of a transgenic animal, and the second cell is constructed in vitro and transferred into the same transgenic animal. In other embodiments, the second cell is an endogenous cell of a transgenic animal and the first cell is constructed in vitro and transferred into the same transgenic animal. Alternatively, the in vivo labeling can be performed by constructing the first cell, the second cell, or both in vitro and transferring the cell(s) into a subject, which can be a mouse, a rabbit, a rat, or a monkey.

In any of the intercellular labeling methods described herein, the peptide comprising the sortase recognition sequence is administered to the transgenic animal or subject, when the method is performed in vivo. In some embodiments, the contacting step between the first cell and the second cell is carried out in a germinal center.

In any of the intercellular labeling methods described herein, the contacting step can be performed in the presence of a candidate compound. Such a method may further comprise assessing whether the candidate compound modulates the interaction between the two members of the receptor-ligand pair, wherein a change of the labeling of the first cell in the presence of the candidate compound indicates that the compound is a modulator of the receptor-ligand pair. Such a method may be useful in drug discovery or design.

In another aspect, the present disclosure provides a nucleic acid comprising a nucleotide sequence that encodes a polypeptide comprising a sortase and a member of a ligand-receptor pair, the encoded polypeptide (which may further comprise a protein tag), a vector (e.g., an expression vector) comprising the nucleic acid, and a host cell comprising any of the vectors described herein. The sortase, sortase recognition sequence, and sortase acceptor peptide can be any of those described herein or know in the art.

In some embodiments, the intercellular labeling method described herein is applied to determine the antigen specificity of a T cell receptor. In such a method, the first cell is an antigen-presenting cell (APC) that expresses a MHC class I molecule, a MHC class II molecule, or both; and the second cell is a T cell that expresses a T cell receptor (TCR). Examples of APCs include, but are not limited to, B cells, dendritic cells, macrophages, or a combination thereof.

In some examples, the APC is engineered to further express a polypeptide encoded by a member of a cDNA library. For example, step (i) may be performed by providing a plurality of APCs which collectively express polypeptides encoded by the cDNA library; and step (iii) may be performed by contacting the plurality of the APCs with the T cell in the presence of the sortase substrate. The method may further comprise isolating the labeled APC produced in step (iii). The member of the cDNA library carried by the labeled APC may be identified for determining antigen specificity of the TCR expressed on the T cell.

In yet another aspect, the present disclosure provides kits for intercellular labeling, comprising: (i) a first cell expressing a first polypeptide, which comprises a sortase acceptor peptide (e.g., an oligoglycine as described herein such as $G_5$), and optionally one member of a receptor-ligand pair (e.g., those described herein), wherein the sortase acceptor peptide is located at the N-terminus of the first polypeptide; and (ii) a second cell expressing a second polypeptide, which comprises a sortase (e.g., any of the sortases disclosed herein, such as a sortase A or a mutant sortase A) or an active fragment thereof, and optionally the other member of the receptor-ligand pair. In some instances, the first polypeptide is a fusion polypeptide comprising both the sortase acceptor peptide and one member of the receptor-ligand pair. Alternatively or in addition, the second polypeptide is a fusion polypeptide comprising both the sortase or an active fragment thereof and the other member of the receptor-ligand pair. Optionally, the kit may further comprise a labeled sortase substrate as described herein. The first polypeptide and/or the second polypeptide may further comprise a protein tag. The first cell, the second cell, or both can be immune cells, such as T cells, B cells, dendritic cells, macrophages, or natural killer cells. In one example, the first cell is an antigen presenting cell (e.g., a B cell, a DC, or a macrophage) and the second cell is a T cell. In another example, the first cell is a T cell and the second cell is a B cell.

In one example, the first polypeptide comprises CD40 and oligoglycine GGGGG (SEQ ID NO: 3), which is located at the N-terminus of the first polypeptide, and the second polypeptide comprises CD40L, which is fused to the sortase at the C-terminus. The first cell may be a B cell, and the second cell may be a T cell.

In another example, the kit is useful in determining TCR specificity, which may comprise (i) a plurality of antigen-presenting cells (APCs) such as B cells, DCs, or macrophages, each expressing one or both of MHC class I and MHC class II molecules and a polypeptide comprising a sortase acceptor peptide, and collectively polypeptides encoded by a cDNA library; (ii) a T cell expressing a polypeptide comprising a sortase or an active fragment thereof; and optionally (iii) a labeled sortase substrate as described herein.

Also disclosed herein is a non-human animal comprising: (i) a first cell expressing a first polypeptide, which comprises a sortase acceptor peptide and optionally one member of a receptor-ligand pair, wherein the sortase acceptor peptide is located at the N-terminus of the first polypeptide; (ii) a second cell expressing a second polypeptide, which comprises a sortase and optionally the other member of the receptor-ligand pair, or (i) and (ii). In some examples, the first cell, the second cell, or both are immune cells, including, but not limited to, T cells, B cells, dendritic cells, macrophages, or natural killer cells. In one example, the first cell is a T cell, and the second cell is a B cell, or vice versa.

In some embodiments, the non-human animal is a transgenic animal, in which a gene encoding the first polypeptide, a gene encoding the second polypeptide, or both are inserted into the genome of the animal. Alternatively, the animal is (a) a transgenic animal, in which a nucleic acid sequence encoding the sortase acceptor peptide is inserted into the endogenous locus encoding the one member of the ligand-receptor pair, leading to the expression of the first polypeptide; or (b) the animal is a transgenic animal, in which a nucleic acid sequence encoding the sortase is inserted into the endogenous locus encoding the other member of the ligand-receptor pair, leading to the expression of the second polypeptide. Examples of transgenic animals include, but are not limited to, transgenic mouse, rat, or rabbit.

In some examples, the animal is a transgenic animal, in which the gene encoding the first polypeptide is inserted into the genome of the animal, and the second cell that expresses the second polypeptide can be transferred into the animal. The second cell may be constructed in vitro. Alternatively, the animal is a transgenic animal, in which the gene encoding the second polypeptide is inserted into the genome of the animal, and the first cell that expresses the first polypeptide is constructed in vitro and transferred into the animal.

In one exemplary non-human animal as described herein, the first polypeptide comprises CD40, which is fused to acceptor peptide GGGGG (SEQ ID NO: 3), and the second polypeptide comprises CD40L, which is fused to the sortase at the C-terminus. The first cell may be a B cell and the second cell may be a T cell.

In some embodiments, the non-human animal can be a transgenic non-human mammal (e.g., a transgenic mouse or transgenic rat) that comprises one or more human immunoglobulin genes or a portion thereof. In other embodiments, the non-human mammal comprises a humanized immune system.

Further, the present disclosure provides methods for identifying a B cell expressing a high affinity B cell receptor (BCR) to an antigen, the method comprising: (i) providing a mammal that comprises (a) a plurality of B cells expressing a first polypeptide, which comprises a sortase acceptor peptide, wherein the sortase acceptor peptide is located at the N-terminus of the first polypeptide, and (b) a plurality of T cells expressing a second polypeptide, which comprises a sortase or an active fragment thereof; (ii) administering to the animal an effective amount of a peptide comprising a sortase recognition sequence, wherein the peptide is associated with a detectable label; (iii) isolating lymphocytes from a germinal center of the animal; and (iv) identifying a B cell that is conjugated to the detectable label, wherein the B cell thus identified expresses a high affinity BCR to an antigen. The animal may be immunized with an antigen of interest. In some examples, the first polypeptide comprises the sortase acceptor peptide fused to a member of a receptor-ligand pair, the member being a B cell protein (i.e., a protein expressed in naturally-occurring B cells). Alternatively or in addition, the second polypeptide comprises the sortase or the active fragment thereof fused to the other member of the receptor-ligand pair, the other member being a T cell protein (i.e., a protein expressed in naturally-occurring T cells).

In some examples, the mammal is a transgenic mammal, in which a gene encoding the first polypeptide, a gene encoding the second polypeptide, or both are inserted into the genome of the mammal. In other examples, the mammal is a transgenic animal, in which a nucleic acid sequence encoding the sortase acceptor peptide is inserted into the endogenous locus encoding the one member of the ligand-receptor pair, leading to the expression of the first polypeptide. Alternatively, the mammal is a transgenic animal, in which a nucleic acid sequence encoding the sortase is inserted into the endogenous locus encoding the other member of the ligand-receptor pair, leading to the expression of the second polypeptide.

In some examples, the mammal is a transgenic mammal, in which the gene encoding the first polypeptide is inserted into the genome of the mammal and expressed on naïve B cells and the plurality of T cells that expresses the second polypeptide, which may be constructed in vitro, are transferred into the mammal.

Examples of transgenic animals include transgenic mouse, transgenic rat, or transgenic rabbit. Exemplary receptor-ligand pairs include CD40 and CD40L, CD80 and CD28, CD80 and CTLA4, CD86 and CD28, CD86 and CTLA4, PD-1 and PD-L1, PD-1 and PD-L2, and ICOS and ICOSL. In one example, the transgenic animal is a transgenic mouse expressing a fusion protein comprising CD40L and SrtA. The nucleotide sequence encoding the SrtA may be inserted downstream of the last coding exon of the endogenous CD40L gene. In another example, the transgenic animal is a transgenic mouse expressing a fusion protein comprising a G5 fragment and CD40. The nucleotide sequence encoding the five glycine fragment may be inserted in the second exon of the endogenous CD40 gene.

The methods described herein may further comprise isolating one or more nucleic acid encoding at least a portion of a heavy chain variable region, at least a portion of a light chain variable region, or both of the B cell receptor (BCR) from the B cell that is conjugated to the detectable label. The at least a portion of the heavy chain variable region, the at least a portion of the light chain variable region, or both encode at least one complementarity determining region of the BCR. Further, the method may also comprise sequencing the at least a portion of the heavy chain variable region, the at least a portion of the light chain variable region, or both.

Any of the methods described herein may further comprise producing a hybridoma cell derived from the B cell that is conjugated to the detectable label, wherein the hybridoma cell produces high affinity antibodies to the antigen. The hybridoma cell thus produced can be cultured in vitro for producing the high affinity antibodies.

In some embodiments, the non-human mammal is a transgenic non-human mammal that comprise human immunoglobulin genes. Examples of such non-human mammals include transgenic mice or transgenic rats. Alternatively, the non-human mammal may comprise a humanized immune system.

Moreover, the present disclosure provides a method for identifying a binding partner of a protein of interest, which may be performed in vitro. Such a method comprising: (i) providing a first population of cells expressing a plurality of polypeptides, each of the cells expressing on its surface a sortase acceptor peptide and a candidate protein, (ii) providing a second population of cells expressing a polypeptide, the cells expressing on the cell surface a sortase, or an active fragment thereof, and the protein of interest; (iii) contacting the first population of cells with the second population of cells in the presence of a peptide comprising a sortase recognition sequence, wherein the peptide is associated with a detectable label; (iv) detecting labeling of cells in the first population of cells; and (v) identifying a binding partner of the protein of interest, wherein a candidate protein is a binding partner of the protein of interest, if the cell that expresses a polypeptide comprising the candidate protein is labeled in step (iii). The polypeptide comprising the protein of interest, the polypeptides comprising the candidate proteins, or both may further comprise a protein tag. In some examples, the sortase acceptor peptide and the protein candidate may be covalently linked to form a fusion polypeptide. Alternatively or in addition, the sortase or the active fragment thereof and the protein of interest are covalently linked to form a fusion polypeptide.

In some examples, the protein of interest is a receptor of an immune cell, e.g., a T cell, a B cell, dendritic cells, macrophages, or natural killer cells. In some examples, the detectable label is biotin or a fluorescent dye.

In any of the methods described herein, the sortase can be a sortase A, a sortase B, a sortase C, or a sortase D. In some examples, the sortase is a mutant SrtA that exhibits improved catalytic activity as compared to the wild-type counterpart, e.g., those described herein. Alternatively or in addition, the sortase recognition sequence is LPXTG (SEQ ID NO: 1), in which X is any amino acid residue. In one example, the sortase recognition sequence is LPETG (SEQ ID NO: 2), which may be co-used with a mutant SrtA as described herein.

Alternatively or in addition, the sortase acceptor peptide is an oligoglycine, which may consist of 1-5 glycine residues.

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

Figure 1:
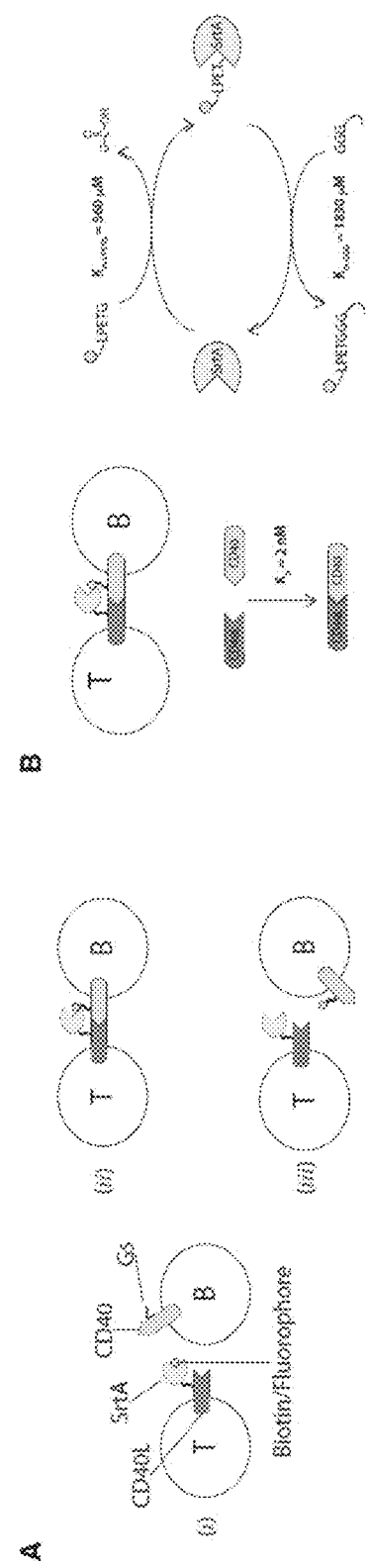
FIG. 1. Schematic representation of intercellular labeling strategy. (A) a schematic illustration showing an exemplary model of SrtA mediated labeling strategy applied to CD40/CD40L ligand/receptor pair. (i) CD40L has been fused to SrtA while its partner, CD40, has been functionalized with five glycine residues. Biotinylated or fluorescently labeled SrtA substrate will bind to the enzyme and form a covalent intermediate. (ii) Upon CD40-CD40L interaction, spatial proximity allows the labeled substrate to be transferred to the N-terminus glycine of CD40. (iii) A cell carrying G5-CD40 maintains the label after CD40L interaction. (B) Kinetic parameters of CD40-CD40L interaction (Kd) and SrtA mediated transpeptidation (KmLPETG (SEQ ID NO: 2); KmGGG). Sequences, from left to right and top to bottom, correspond to SEQ ID NOs.: 2, 54, and 55.

Effective humoral immune response requires the production of antibodies that bind with high affinity and specificity to the antigen. The generation of high-affinity antibodies takes place in germinal centers (GCs), specialized anatomic structures within lymph nodes. There, B cells exhibiting randomly mutated immunoglobulin molecules (BCRs) at the plasma membrane are selected based on their affinity for the antigen. Recent studies on the cellular mechanism mediating affinity-based selection of B cells revealed a key role of the interaction between B cells and follicular T helper cells (Tfh). Despite the emerging role of this interaction in the generation of high-affiniity antibody, the molecular events beyond this process are poorly characterized.

The present disclosure is based, at least in part, on the development of a novel approach to track interactions between cells, such as immune cells, in vitro (e.g., using cell lines), ex vivo (e.g., using primary murine lymphocytes), and/or in vivo (e.g., in mice), based on the enzymatic labeling of receptor and ligand molecules oriented across the immunological synapse. The present study has achieved intercellular labeling between cultured T cells and B cells in vitro, primary murine B and T cells ex vitro, and B cells and T cells in vivo. It was also demonstrated that the labeling occurs upon interaction between several ligand-receptor pairs, and that labeling intensity depends on ligand-receptor affinity; labeling between non interacting molecules occurs at low levels, in the context of cognate interaction. By cell transfer, it has been demonstrated that enzymatic activity required for intercellular labeling is maintained in vivo, and that enzyme substrate can easily delivered to secondary lymphoid organs. This system would allow for determining the molecular signature triggered in B cells by the interaction with Tfh cells in vivo and to identify the key factors and pathways that control affinity-based selection of B cells in the GC. Moreover, this system has the potential as a broadly useful tool for tracking cell-cell interactions in vivo that can be applied to most biological areas. Further, the intercellular labeling system described herein can be applied to identify particular antigens to which a T cell receptor of unknown specificity responds. This would be useful to identify the particular antigens that stimulate T cell responses in various diseases, such as cancer, infection, and autoimmune diseases. One could, for example, isolate T cells from a disease site, e.g., a cancer site, a site of infection, or an affected site of an autoimmune disease, and identify the antigens to which the involved T cells respond. The antigens thus identified might be useful as, e.g., vaccine antigens.

Accordingly, described herein are intercellular labeling methods and uses of such labeling methods to track ligand-receptor interactions both in vitro and in vivo, to identify compounds capable of modulating ligand-receptor interaction, to identify potential binding partners of proteins of interest, or to identify cognate antigens for TCRs with unknown specificities.

I. Intercellular Labeling Mediated by Ligand-Receptor Interaction

The intercellular labeling method described herein involves two types of engineered cells. The first type of cell is engineered to express on the cell surface a polypeptide comprising a sortase or an active fragment thereof. The second type of cell is engineered to express on the cell surface a polypeptide comprising a sortase acceptor peptide (e.g., oligoglycine), which is located at the N-terminus of the polypeptide. These two cells can interact with each other via, e.g., a receptor-ligand pair expressed on the surface of the cells, to bring the two cells together. The sortase acceptor peptide and/or the sortase/active fragment thereof may or may not be fused to the receptor and ligand, respectively. Upon interaction, the spatial proximity of the two cells would allow for the sortase or the active fragment thereof expressed on the second type of cell to transfer a sortase substrate onto the sortase acceptor expressed on the first type of cell. Accordingly, the two cells can be incubated in the presence of a labeled peptide comprising a sortase recognition sequence, which binds to the polypeptide comprising a sortase expressed on the surface of one cell, to label the cell expressing the sortase acceptor peptide. A schematic illustration of this intercellular labeling method is provided in FIG. 1.

(i) Sortase-Mediated Cell Surface Labeling

Described herein are sortase-mediated cell surface labeling methods, which allow for tracking molecule interactions both in vitro and in vivo.

(a) Sortase

Sortases are a family of enzymes capable of carrying out a transpeptidation reaction conjugating the C-terminus of a protein to the N-terminus of another protein via transamidation. Sortases are also referred to as transamidases, and typically exhibit both a protease and a transpeptidation activity. Various sortases from prokaryotic organisms have been identified. For example, some sortases from Gram-positive bacteria cleave and translocate proteins to proteoglycan moieties in intact cell walls. Among the sortases that have been isolated from *Staphylococcus aureus*, are sortase A (Srt A) and sortase B (Srt B). Thus, in certain embodiments, a transamidase used in accordance with the intercellular labeling methods described herein is a sortase A, e.g., from *S. aureus*, also referred to herein as SrtAaureus. In other embodiments, a transamidase is a sortase B, e.g., from *S. aureus*, also referred to herein as SrtBaureus.

Sortases have been classified into four classes, designated A, B, C, and D (i.e., sortase A, sortase B, sortase C, and sortase D, respectively) based on sequence alignment and phylogenetic analysis of 61 sortases from Gram-positive bacterial genomes (Dramsi et al., *Res Microbiol.* 156(3): 289-97, 2005; the entire contents of which are incorporated herein by reference). These classes correspond to the following subfamilies, into which sortases have also been classified by Comfort and Clubb (Comfort et al., *Infect Immun.*, 72(5):2710-22, 2004; the entire contents of which are incorporated herein by reference): Class A (Subfamily 1), Class B (Subfamily 2), Class C (Subfamily 3), and Class D (Subfamilies 4 and 5). The aforementioned references disclose numerous sortases and their recognition motifs. See also Pallen et al., TRENDS in *Microbiology*, 2001, 9(3), 97-101; the entire contents of which are incorporated herein by reference). Those skilled in the art will readily be able to assign a sortase to the correct class based on its sequence and/or other characteristics such as those described in Drami, et al., supra.

The term "sortase A" is used herein to refer to a class A sortase, usually named SrtA in any particular bacterial species, e.g., SrtA from *S. aureus*. Likewise "sortase B" is used herein to refer to a class B sortase, usually named SrtB in any particular bacterial species, e.g., SrtB from *S. aureus*. The present disclosure encompasses embodiments relating to any of the sortase classes known in the art (e.g., a sortase A from any bacterial species or strain, a sortase B from any bacterial species or strain, a class C sortase from any bacterial species or strain, and a class D sortase from any bacterial species or strain).

In some embodiments, the sortase used in the intercellular labeling methods described herein is a wild-type enzyme. In other embodiments, the sortase is a modified version which may possess a superior feature as compared to the wild-type counterpart (e.g., higher catalytic activity). In some examples, the sortase can be a mutant of SrtA, which may comprise one or more of the following positions: P94, S102, A104, E105, K138, K152, D160, K162, T164, D165, K173, I182, K190, and K196. For example, a SrtA mutant may comprise one or more of the following mutations: P94R or P94S, S102C, A104H, E105D, K138P, K152I, D160K or D160N, K162H, T164N, D165A, K173E, I182V, K190E, and K196S or K196T. In one example, the sortase is a triple mutant P94S/D160N/K196T of SrtA from *S. aureus*.

In other embodiments, modified sortase having altered substrate specificity can be used in the intercellular labeling methods described herein. For example, sortase A mutants having one or more mutations at positions S102 (e.g., S102C), A104 (e.g., A104H or A104V), E105 (e.g., E105D), K138 (e.g., K138P), K152 (e.g., K152I), N162 (e.g., N162N), T164 (e.g., T164N), K173 (e.g., K173E), I182 (e.g., I182V), T196 (e.g., T196S), N98 (e.g., N98D), A118 (e.g., A118T), F122 (e.g., F122A), K134 (e.g., K134R), F144 (e.g., F144L), and E189 (e.g., E189F). Such a modified sortase may recognize sequences such as LAXTG (SEQ ID NO: 6) and/or LPXSG (SEQ ID NO: 7), in which X can be any amino acid residue. Examples include mutant S102C/A104H/E105D/K138P/K152I/N162N/T164N/K173E/I182V/T196S, and mutant N98D/A104V/A118T/F122A/K134R/F144L/E189F. Additional sortase mutants having altered substrate specificity are disclosed in US20140057317 and Dorr et al., *PNAS* 111 (37):13343-13348 (2014), the relevant disclosures therein are incorporated by reference herein.

A modified version of a wild-type sortase may share at least 85% (e.g., 90%, 95%, 98%, or above) sequence identity to the wild-type counterpart. It may contain mutations at one or more positions corresponding to those described above, which can be identified by analyzing the amino acid sequence of a wild-type sortase with the amino acid sequence of a SrtA. The "percent identity" of two amino acid sequences can be determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some embodiments, the intercellular labeling methods can use an active fragment of a sortase. Such a fragment of a specific sortase can be identified based on knowledge in the art or by comparing the amino acid sequence of that sortase with a sortase having known structure/function correlation (e.g., active domain being identified). In some examples, the sortase used herein can be an active fragment of a sortase A such as SrtA from *S. aureus*, e.g., a sortase A fragment lacking the N-terminal 59 or 60 amino acid residues, or a functional variants thereof, which may contain one or more of the mutations described herein.

Amino acid sequences of Srt A and Srt B and the nucleotide sequences that encode them are known to those of skill in the art and are disclosed in a number of references cited herein, the entire contents of all of which are incorporated herein by reference. See, e.g., GenBank accession numbers NP_375640 and YP_043193. The amino acid sequences of *S. aureus* SrtA and SrtB are homologous, sharing, for example, 22% sequence identity and 37% sequence similarity. The amino acid sequence of a sortase-transamidase from *Staphylococcus aureus* also has substantial homology with sequences of enzymes from other Gram-positive bacteria, and such transamidases can be utilized in the ligation processes described herein. For example, for SrtA there is about a 31% sequence identity (and about 44% sequence similarity) with best alignment over the entire sequenced region of the *S. pyogenes* open reading frame. There is about a 28% sequence identity with best alignment over the entire sequenced region of the *A. naeslundii* open reading frame. It will be appreciated that different bacterial strains may exhibit differences in sequence of a particular polypeptide, and the sequences herein are exemplary.

In certain embodiments a transamidase bearing 18% or more sequence identity, 20% or more sequence identity, or 30% or more sequence identity with an *S. pyogenes, A. naeslundii, S. mutans, E. faecalis* or *B. subtilis* open reading frame encoding a sortase can be screened, and enzymes having transamidase activity comparable to Srt A or Srt B from *S. aureus* can be utilized (e.g., comparable activity sometimes is 10% of Srt A or Srt B activity or more).

In some embodiments, the intercellular labeling methods described herein use a sortase A (SrtA) or an active fragment thereof. SrtA recognizes the motif LPXTX; wherein each occurrence of X represents independently any amino acid residue), with common recognition motifs being, e.g., LPKTG (SEQ ID NO: 8), LPATG (SEQ ID NO: 9), or LPNTG (SEQ ID NO: 10). In some embodiments LPETG (SEQ ID NO: 2) is used as the sortase recognition motif. However, motifs falling outside this consensus may also be recognized. For example, in some embodiments the motif comprises an 'A' rather than a 'T' at position 4, e.g., LPXAG (SEQ ID NO: 11), or LPNAG (SEQ ID NO: 12). In some embodiments the motif comprises an 'A' rather than a 'G' at position 5, e.g., LPXTA (SEQ ID NO: 13), or LPNTA (SEQ ID NO: 14). In some embodiments the motif comprises a 'G' rather than 'P' at position 2, e.g., LGXTG (SEQ ID NO: 15) or LGATG (SEQ ID NO: 16). In some embodiments the motif comprises an 'I' rather than 'L' at position 1, e.g., IPXTG (SEQ ID NO: 17), IPNTG (SEQ ID NO: 18) or IPETG (SEQ ID NO: 19). Additional suitable sortase recognition motifs will be apparent to those of skill in the art, and the invention is not limited in this respect. It will be appreciated that the terms "recognition motif" and "recognition sequence", with respect to sequences recognized by a transamidase or sortase, are used interchangeably. In some embodiments, the SrtA is a mutant as described herein, which may possess improved enzymatic activity relative to the wild-type counterpart. Such a mutant may recognize LAETG (SEQ ID NO: 20) and use a peptide comprising the recognition sequence as a substrate. Such sortase recognition motifs can be used in any of the methods described herein.

In some embodiments of the invention the sortase is a sortase B (SrtB) or an active fragment thereof, e.g., a sortase B of *S. aureus, B. anthracis*, or *L. monocytogenes*. Motifs recognized by sortases of the B class (SrtB) often fall within the consensus sequences NPXTX, e.g., NP[Q/K]-[T/s]-[N/G/s] (SEQ ID NO: 21), such as NPQTN (SEQ ID NO: 22) or NPKTG (SEQ ID NO: 23). For example, sortase B of *S. aureus* or *B. anthracis* cleaves the NPQTN (SEQ ID NO: 22) or NPKTG (SEQ ID NO: 23) motif of IsdC in the respective bacteria (see, e.g., Marraffini et al., Journal of Bacteriology, 189(17): 6425-6436, 2007). Other recognition motifs found in putative substrates of class B sortases are NSKTA (SEQ ID NO: 24), NPQTG (SEQ ID NO: 25), NAKTN (SEQ ID NO: 26), and NPQSS (SEQ ID NO: 27). For example, SrtB from *L. monocytogenes* recognizes certain motifs lacking P at position 2 and/or lacking Q or K at position 3, such as NAKTN (SEQ ID NO: 26) and NPQSS (SEQ ID NO: 27) (Mariscotti et al., J Biol Chem. 2009 Jan. 7). Such sortase recognition motifs can also be used in any of the methods described herein.

Using sortases with distinct substrate specificity, it is possible to combine N-terminal and C-terminal labeling strategies (Antos et al., 2009, *J. Am. Chem. Soc.*, 131(31): 10800-10801) to generate multi-labeled cells. For example, unlike Sortase A from *Staphylococcus aureus*, Sortase A derived from *Streptococcus pyogenes* recognizes LPXTA (SEQ ID NO: 13) motifs and accepts oligo-alanine probes as nucleophiles. Therefore, the sortase reactions of both enzymes can be performed as orthogonal reactions. Utilization of such sortase reactions with suitable sortase(s) is also within the scope of the present disclosure.

In some embodiments, the sortase is a sortase C (Srt C) or an active fragment thereof. Sortase C may utilize LPXTX as a recognition motif, with each occurrence of X independently representing any amino acid residue. This recognition motif can be used for constructing the sortaggable surface proteins described herein.

In yet other embodiments, the sortase is a sortase D (Srt D) or an active fragment thereof. Sortases in this class are predicted to recognize motifs with a consensus sequence NA-[E/A/S/H]-TG (SEQ ID NO: 28; Comfort D, supra). Sortase D has been found, e.g., in *Streptomyces* spp., *Corynebacterium* spp., *Tropheryma whipplei, Thermobifida fusca*, and *Bifidobacterium longhum*. LPXTA (SEQ ID NO: 13) or LAXTG (SEQ ID NO: 6) may serve as a recognition sequence for sortase D, e.g., of subfamilies 4 and 5, respectively subfamily-4 and subfamily-5 enzymes process the motifs LPXTA (SEQ ID NO: 13) and LAXTG (SEQ ID NO: 6), respectively. For example, *B. anthracis* Sortase C has been shown to specifically cleave the LPNTA (SEQ ID NO: 14) motif in *B. anthracis* BasI and BasH (see Marrafini, supra).

Additional sortases and their active fragments, including, but not limited to, sortases recognizing additional sortase recognition motifs are also suitable for use in some embodiments of this invention. For example, sortases described in Chen et al., *Proc Natl Acad Sci USA*. 2011 Jul. 12; 108(28): 11399 (the entire contents of which are incorporated herein); and a sortase that recognizes QVPTGV (SEQ ID NO: 29) motif as described in Barnett et al., *Journal of Bacteriology*, Vol. 184, No. 8, p. 2181-2191, 2002 (the entire contents of which are incorporated herein by reference).

The use of sortases found in any gram-positive organism, such as those mentioned herein and/or in the references (including databases) cited herein is contemplated in the context of some embodiments of this invention. Also contemplated is the use of sortases found in gram negative bacteria, including, but not limited to, *Colwellia psychrerythraea, Microbulbifer degradans, Bradyrhizobium japonicum, Shewanella oneidensis*, and *Shewanella putrefaciens*. Such sortases recognize sequence motifs outside the LPXTX consensus, for example, LP[Q/K]T[A/S]T (SEQ ID NO: 30). In keeping with the variation tolerated at position 3 in sortases from gram-positive organisms, a sequence motif LPXT[A/S] (SEQ ID NO: 31), e.g., LPXTA (SEQ ID NO: 13) or LPSTS (SEQ ID NO: 32) may be used.

(b) Sortase-Catalyzed Transpeptidation Reaction

Sortase-catalyzed transacylation reactions, and their use in transpeptidation (sometimes also referred to as transacylation) for protein engineering are well known to those of skill in the art (see, e.g., Ploegh et al., WO/2010/087994, and Ploegh et al., WO/2011/133704, the entire contents of which are incorporated herein by reference). In general, the transpeptidation reaction catalyzed by sortase results in the conjugation of a first protein containing a C-terminal sortase recognition motif, e.g., LPXTX; wherein each occurrence of X independently represents any amino acid residue), with a second protein comprising an N-terminal sortase acceptor peptide, e.g., one or more N-terminal glycine residues. In some embodiments, the sortase recognition motif is a sortase recognition motif described herein. In certain embodiments, the sortase recognition motif is LPXT or LPXTG (SEQ ID NO: 1).

The sortase transacylation reaction provides means for efficiently linking an acyl donor with a nucleophilic acyl acceptor. This principle is widely applicable to many acyl donors and a multitude of different acyl acceptors. Previously, the sortase reaction has been employed for ligating proteins and/or peptides to one another, ligating synthetic peptides to recombinant proteins, linking a reporting molecule to a protein or peptide, joining a nucleic acid to a protein or peptide, conjugating a protein or peptide to a solid support or polymer, and linking a protein or peptide to a label. Such products and processes save cost and time associated with ligation product synthesis and are useful for conveniently linking an acyl donor to an acyl acceptor.

Sortase-mediated transpeptidation reactions (also sometimes referred to as transacylation reactions) are catalyzed by the transamidase activity of sortase, which forms a peptide linkage (an amide linkage), between an acyl donor compound and a nucleophilic acyl acceptor containing an $NH_2$—$CH_2$-moiety.

(ii) Engineered Cells Expressing Sortase-Ligand/Sortase Acceptor-Receptor Fusion Polypeptides The intercellular labeling methods described herein involve at least two cells, one of which is engineered to express on the surface a sortase acceptor peptide and the other of which is engineered to express a sortase or an active fragment thereof on the surface.

To facilitate surface expression, the sortase acceptor peptide and/or the sortase/active fragment thereof may be fused to a transmembrane domain, and optionally a hinge domain. Exemplary transmembrane domains include, but are not limited to, a transmembrane of a single-pass membrane protein, e.g., CD8α, CD8β, 4-1BB, CD28, CD34, CD4, FcεRIγ, CD16 (e.g., CD16A or CD16B), OX40, CD3ζ, CD3ε, CD3γ, CD3δ, TCRα, CD32 (e.g., CD32A or CD32B), CD64 (e.g., CD64A, CD64B, or CD64C), VEGFR2, FAS, and FGFR2B. Alternatively, the transmembrane domain may be a non-naturally occurring hydrophobic protein segment. The hinge domain may be a hinge domain from CD8α or from an immunoglobulin molecule. It is expected that the physical interaction will be sufficiently stable and specific to allow for specific labeling of the cells without need for the sortase and sortase acceptor peptides to be fused to members of a particular interacting receptor-ligand pair.

The cells for use in the labeling methods described herein can be any type of cells capable of expressing proteins on cell surfaces. Examples include, but not limited to, bacterial cells, yeast cells, insect cells, plant cells, avian cells (e.g., chicken cells), and mammalian cells (e.g., mouse, rat, rabbit, camelid, non-human primate, human). The at least two cells involved in the labeling methods can be of the same type. Alternatively, they can be different types of cells.

In some embodiments, the cells can be immune cells, including, but not limited to, T cells, B cells, dendritic cells, macrophages, natural killer cells, neutrophils, basophils, monocytes, and eosinophils. Examples of T cells include, but are not limited to, CD4$^+$ T cells (also known as T helper cells or Th cells, including $T_H1$, $T_H2$, $T_H3$, $T_H17$, Th9, and follicular T helper cells or Tfh cells), CD8$^+$ cells (also known as cytotoxic cells or CTLs), memory T cells, and regulatory T cells ($T_{reg}$ cells). The B cells used in the method described herein can be a B cell of any development stage (including progenitor B cells, early pro-B cells, late pro-B cells, large pre-B cells, small pre-B cells, immature B cells, and mature B cells), or any type of B cells (including plasma B cells, memory B cells, B-1 cells, B-2 cells, marginal-zone B cells, follicular B cells, and regulatory B cells). In one example, one cell can be a T cell and the other cell can be a B cell, a dendritic cell, or a macrophage. Alternatively, one cell can be a B cell and the other cell can be a T cell, a dendritic cell, or a macrophage. Additional examples include the combination of T cell/T cell, T cell/B cell, B cell/B cell, T cell/dendritic cell, T cell/macrophage cell, B cell/dendritic cell, and B cell/macrophage cell.

In some embodiments, one or both cells are a hematological or hematopoietic cell.

In some embodiments, one or both of the cells can be a diseased cell, for example, a cancer cell, including, but not limited to, a breast cancer cell, a lung cancer cell, a liver cancer cell, a kidney cancer cell, an oral cancer cell, a skin cancer cell, a cervical cancer cell, an ovarian cancer cell, a pancreatic cancer cell, a brain tumor cell, a melanoma cell, a colon cancer cell, a leukemia cell, or a lymphoma cell. Alternatively, one or both of the cells can be a normal cell of any type or derived from any tissue, including, but not limited to, breast cell, lung cell, liver cell, kidney cell, skin cell, cervical cell, ovarian cell, pancreatic cell, brain cell, or blood cell.

The interaction between the two engineered cells described herein may be mediated by a receptor-ligand pair, each of which is expressed on the surface of one of the two engineered cells. The receptor, the ligand, or both may be endogenous to the engineered cells. Alternatively, they can be exogenous to the cells. In the latter case, expression vectors carrying genes encoding the receptor or the ligand can be constructed via conventional technology and introduced into the cells for surface expression. In some embodiments, the receptor, the ligand, or both are expressed on the surface of the cells at a high level to improve the stability of the cell-cell interaction. In some embodiments, either or both members of the receptor-ligand pair are ones whose cell surface expression is upregulated upon a cognate interaction (e.g., upon MHC:TCR recognition where the MHC molecule displays a peptide recognized by the TCR).

In some embodiments, the polypeptide comprising the sortase acceptor peptide and a member of the receptor-ligand pair can be expressed on the surface of the first type of engineered cells as separate polypeptides. The polypeptide comprising the sortase or the active fragment thereof and the other member of the receptor-ligand pair can also be express on the surface of the second type of cells as separate polypeptides.

In other embodiments, the sortase acceptor peptide and the member of the receptor-ligand pair can be covalently linked to form a single, fusion polypeptide, which is expressed on the surface of the first type of cell. The sortase or the active fragment thereof and the other member of the receptor-ligand can also be linked covalently to form a fusion polypeptide, which is expressed on the surface of the second type of cell.

As used herein, a "ligand-receptor pair" refers to a pair of molecules (e.g., biological molecules) that have a specific affinity for each other. One member of the receptor-ligand pair may be localized on the surface of a cell, and preferably on the surface of the plasma membrane, at some point in its existence in vivo. Within a given receptor-ligand pair, either member may be considered to be the ligand or the receptor. Examples of ligand-receptor pairs include, but are not limited to, a cell surface receptor and its ligand, (e.g., an oncogene-encoded receptor and its ligand, a growth factor and its receptor, such as a lymphokine and its receptor or an interleukin and its receptor); an enzyme and its substrate; an enzyme and a specific inhibitor or other non-catalyzable substrate of the enzyme; a hormone and its receptor; a first subunit of a multimeric protein and a second subunit of the multimeric protein, (for example, two subunits of an immunoglobulin molecule); a polypeptide portion of a protein and a non-peptide cofactor of the protein; a molecule involved in cellular adhesion, such as a carbohydrate involved in cell adhesion; a cadherin; a cell adhesion molecule (CAM) (e.g., cell-CAM, neural N-CAM, or muscle N-CAM); a laminin; a fibronectin; or an integrin and the molecule to which it binds, which may or may not be a cellular adhesion molecule; a first component of an organelle, the mitotic or meiotic apparatuses, or other subcellular structure, that displays a specific interaction with a second component of the same structure or a related structure; a lectin and a carbohydrate; a toxin and its receptor (e.g., diphtheria toxin and its cell surface receptor); a component of a virus and its cell surface receptor; or, an IgE molecule and an IgE receptor (e.g., the IgE receptor found on mast cells, or any other Ig molecule and its receptor).

In some embodiments, a ligand-receptor pair used in the intercellular labeling methods described herein are naturally-occurring ligand-receptor pair. Alternatively, one or both of the members of a ligand-receptor pair may be a modified version of a naturally-occurring molecule; the modified version may have improved or decreased binding activity to the other member of the pair.

In some examples, the ligand-receptor pair used in the labeling methods described herein can be a ligand-receptor pair expressed on immune cells. For example, the ligand-receptor pair can be a T cell co-stimulatory molecule and its ligand, or a B cell receptor and its ligand. Examples include, but are not limited to, CD28/CD80, CD28/CD86, CTLA4/CD80, CTLA4/CD86, CD40/CD40L, PD-1/PD-L1, PD-1/PD-L2, ICOS/ICOSL, OX40/OX40L, CD27/CD27L, and 4-1BB/4-1BBL. Preferably, at least one of the two members of a ligand-receptor pair has its N-terminus exposed to the extracellular or luminal space (e.g., a Type I membrane protein).

CD28 is expressed on T cells (on most CD4$^+$ T cells and some CD8$^+$ T cells) and CTLA4 (also known as CD152) is usually expressed on activated T cells. Their ligands, CD80 and CD86 (also known as B7-1 and B7-2) are usually expressed on antigen presenting cells such as dendritic cells, B cells, and macrophage cells. CD40L (also known as CD154) is expressed on activated T cells and its binding partner, CD40, is expressed on B cells, dendritic cells, macrophages, and endothelial cells. ICOS (also known as CD278) is expressed on activated T cells and its ligand, ICOSL (also known as CD275) is expressed on antigen presenting cells such as B cells, dendritic cells, macrophages, and endothelial cells. Other immune cell ligand-receptor pairs and the type of immune cells on which they express are known in the art. See, e.g., Abbas et al., Cellular and Molecular Immunology, 4$^{th}$ ed., W.B. Saunders Co. (the relevant disclosures therein are incorporated by reference herein).

Members of the ligand-receptor pair used in the labeling methods described herein can be full-length proteins as they exist in nature. Alternatively, one or both members of the ligand-receptor pair can be a fragment of the naturally-occurring ligand-receptor, which may comprise the extracellular domain involved in interacting with its binding partner.

To perform the intercellular labeling methods described herein, one member of any of the ligand-receptor pair as described herein, which has its N-terminus exposed to the extracellular or luminal space, can be fused to a sortase acceptor peptide, which is located at the N-terminus of the fusion polypeptide, via methods known in the art, e.g., recombinant technology. A sortase acceptor peptide can be any peptide that provides a nucleophilic acyl group for accepting a sortase substrate (a peptide comprising a sortase recognition sequence as described herein). Such an acceptor peptide may contain up to about 50 amino acids, such as up to 40, 30, 20, 15, 10, or 5 amino acids. In some embodiments, the acceptor peptide is an oligoglycine or oligoalanine, such as a 1-5 glycine fragment or a 1-5 alanine fragment. In some examples, the oligoglycine consists of 3 or 5 glycine residues. In other examples, the oligoalanine consists of 3 or 5 alanine residues.

The other member of the ligand-receptor pair can be fused to a suitable sortase, e.g., a sortase capable of transferring its substrate onto the sortase acceptor peptide fused to the binding partner. For example, a SrtA of S. aureus can be used when the corresponding acceptor peptide is an oligoglycine. Alternatively, a SrtA of S. pyogenes can be used when the corresponding acceptor peptide is an oligoalanine. In some examples, the sortase is fused to the N-terminus of the member of the ligand-receptor pair. In other examples, the sortase is fused to the C-terminus of the member of the ligand-receptor pair.

In some embodiments, one or both of the fusion polypeptides described herein may further comprise a protein tag, which may be useful for purifying, expressing, solubilizing, and/or detecting a polypeptide. A protein tag may be relatively small, e.g., ranging from a few amino acids up to about 100 amino acids long. Alternatively, a protein tag may be more than 100 amino acids long, e.g., up to about 500 amino acids long, or more. The use of protein tags in recombinant technology is well known in the art. Exemplary protein tags include, but are not limited to, an HA, TAP, Myc, 6xHis, Flag, streptavidin, biotin, or GST tag, to name a few examples. In some embodiments, a protein tag is a solubility-enhancing tag (e.g., a SUMO tag, NUS A tag, SNUT tag, or a monomeric mutant of the Ocr protein of bacteriophage T7). See, e.g., Esposito D and Chatterjee D K. Curr Opin Biotechnol.; 17(4):353-8 (2006). If desired, a protein tag can be cleavable so that it can be removed, e.g., by a protease. In some embodiments, this is achieved by including a protease cleavage site in the tag, e.g., adjacent or linked to a functional portion of the tag. Exemplary proteases include, e.g., thrombin, TEV protease, Factor Xa, and PreScission protease. In some embodiments, a "self-cleaving" tag is used. See, e.g., WO/2005/086654.

Nucleic acids encoding the fusion polypeptides described herein, can be inserted into a suitable vector (e.g., a retroviral vector) using methods well known in the art. Sambrook et al., Molecular Cloning, A Laboratory Manual, 3$^{rd}$ Ed., Cold Spring Harbor Laboratory Press. For example, the gene and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Suitable vectors and methods for producing vectors containing transgenes are well known and available in the art. Sambrook et al., Molecular Cloning, A Laboratory Manual, 3$^{rd}$ Ed., Cold Spring Harbor Laboratory Press.

A "vector" refers to a nucleic acid molecule capable of transporting another nucleic acid to which it has been linked. The vector can be capable of autonomous replication or integrate into a host DNA. Examples of the vector include a plasmid, cosmid, or viral vector. The vectors for use in the methods described herein may include a nucleic acid in a form suitable for expression of the nucleic acid in a host cell. Preferably the vector includes one or more regulatory sequences operatively linked to the nucleic acid sequence to be expressed. The term "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of transcription of RNA desired, and the like.

Selection of a suitable vector may depend on the type of host cell, to which the vector is to be introduced. For example, a bacterial vector may be selected if it is to be introduced into a bacterial cell. In some examples, a viral vector may be used for introducing nucleic acids that encode a fusion polypeptide as described herein into an immune cell (e.g., a T cell, a B cell, a natural killer cell, a dendritic cell, or a macrophage). A "viral vector" as described herein refers to a recombinantly produced virus or viral particle that comprises a polynucleotide to be delivered into a host cell, either in vivo, ex vivo or in vitro. Examples of viral vectors include retroviral vectors such as lentiviral vectors, adenovirus vectors, adeno-associated virus vectors and the like. In aspects where gene transfer is mediated by a retroviral vector, a vector construct refers to the polynucleotide comprising the retroviral genome or part thereof, and a therapeutic gene.

A variety of promoters can be used for expression of a polypeptide described herein, e.g., a polypeptide comprising a sortase/active fragment thereof or a sortase acceptor peptide, which may or may not be fused to a member of a ligand-receptor pair. Promoters that can be used to express the protein are well known in the art. Promoters include cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter and the herpes simplex tk virus promoter.

Regulatable promoters can also be used. Such regulatable promoters include those using the lac repressor from *E. coli* as a transcription modulator to regulate transcription from lac operator-bearing mammalian cell promoters (Brown, M. et al., *Cell*, 49:603-612 (1987)), those using the tetracycline repressor (tetR) (Gossen, et al., *Proc. Natl. Acad. Sci. USA* 89:5547-5551 (1992); Yao, F. et al., Human Gene Therapy, 9:1939-1950 (1998); Shockelt, P., et al., *Proc. Natl. Acad. Sci. USA*, 92:6522-6526 (1995)). Other systems include FK506 dimer, VP16 or p65 using estradiol, RU486, diphenol murislerone or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters (Brown et al., Cell, 49:603-612 (1987)); Gossen and Bujard (1992); Gossen et al., Natl. Acad. Sci. USA, 89:5547-5551 (1992)) combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells transactivator or repressor fusion protein, which in some instances can be toxic to cells (Gossen et al., *Natl. Acad. Sci. USA*, 89:5547-5551 (1992); Shockett et al., *Proc. Natl. Acad. Sci. USA*, 92:6522-6526 (1995)), to achieve its regulatable effects.

The effectiveness of some inducible promoters can be increased over time. In such cases one can enhance the effectiveness of such systems by inserting multiple repressors in tandem, e.g., TetR linked to a TetR by an internal ribosome entry site (IRES). Alternatively, one can wait at least 3 days before screening for the desired function. While some silencing may occur, it can be minimized by using a suitable number of cells, preferably at least $1\times10^4$, more preferably at least $1\times10^5$, still more preferably at least $1\times10^6$, and even more preferably at least $1\times10^7$. One can enhance expression of desired proteins by known means to enhance the effectiveness of this system. For example, using the Woodchuck Hepatitis Virus Posttranscriptional Regulatory Element (WPRE). See Loeb, V. E., et al., Human Gene Therapy 10:2295-2305 (1999); Zufferey, R., et al., J. of Virol. 73:2886-2892 (1999); Donello, J. E., et al., J. of Virol. 72:5085-5092 (1998).

Examples of polyadenylation signals useful to practice the methods described herein include, but are not limited to, human collagen I polyadenylation signal, human collagen II polyadenylation signal, and SV40 polyadenylation signal.

Vectors comprising nucleic acid sequences encoding the fusion polypeptides described herein, which may be operably linked to regulatory elements, may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA, which can integrate into the chromosome, may be introduced into the cell. When introducing DNA into the cell, reagents, which promote DNA integration into chromosomes, may be added. DNA sequences, which are useful to promote integration, may also be included in the DNA molecule. Alternatively, RNA may be introduced into the cell.

Selectable markers can be used to monitor uptake of the desired transgene into the progenitor cells described herein. These marker genes can be under the control of any promoter or an inducible promoter. These are known in the art and include genes that change the sensitivity of a cell to a stimulus such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, and LacZ.

Any of the engineered cells or a combination thereof are also within the scope of the present disclosure.

Any of the intercellular labeling methods described herein may be used to track cell-cell interaction either in vitro or in vivo. Some exemplary utilities are provided below.

(iii) In Vitro Labeling

The intercellular labeling methods may be performed either in vitro or in vivo. In some embodiments, the intercellular labeling methods can be performed in vitro, where the two engineered cells described herein are incubated in a cell culture in the presence of a peptide that comprises a sortase recognition sequence ("sortase substrate"). Such a peptide is conjugated with a detectable label. When the ligand-receptor interact, the resultant spatial proximity would allow for the transfer of the detectable label onto the sortase acceptor peptide via the transpeptidation reaction catalyzed by the sortase, leading to the labeling of the cell that expresses the sortase acceptor peptide.

The sortase substrate used in the methods described herein, which is conjugated to a detectable label, can comprise any sortase recognition sequence as known in the art or disclosed herein. Selection of a suitable sortase recognition sequence would depend on the type of sortase used in the same methods.

For example, when a sortase A is used, the corresponding substrate may comprise the recognition sequence LPXTG (SEQ ID NO: 1), in which X can be any amino acid residue (naturally-occurring or non-naturally occurring), e.g., any of the 20 standard amino acids found most commonly in proteins found in living organisms. Alternatively, the recognition motif can be LPXT, in which X is D, E, A, N, Q, K, or R. In other examples, X is selected from K, E, N, Q, and A in an LPXTG (SEQ ID NO: 1) or LPXT motif, which are recognized by a sortase A. In some examples, a mutant SrtA as described here is used and the corresponding labeled substrate may comprise the motif LPETG (SEQ ID NO: 2). Such mutants may comprise one or more of the following positions: P94, S102, A104, E105, K138, K152, D160, K162, T164, D165, K173, I182, K190, and K196. For example, a SrtA mutant may comprise one or more of the following mutations: P94R S102C, A104H, E105D, K138P, K152I, D160K, K162H, T164N, D165A, K173E, I182V, K190E, and K196S. In one example, the sortase is a triple mutant P94S/D160N/K196T of SrtA from *S. aureus*.

In an example, a sortase substrate comprising the recognition sequence LPXTG (SEQ ID NO: 1) or LPXT, in which X is selected from K, S, E, L, A, and N, can be used when the corresponding sortase is a class C sortase. Exemplary sortase recognition motifs include, but are not limited to, LPKTG (SEQ ID NO: 8), LPITG (SEQ ID NO: 33), LPDTA (SEQ ID NO: 34), SPKTG (SEQ ID NO: 35), LAETG (SEQ ID NO: 20), LAATG (SEQ ID NO: 36), LAHTG (SEQ ID NO: 37), LASTG (SEQ ID NO: 38), LPLTG (SEQ ID NO: 39), LSRTG (SEQ ID NO: 40), LPETG (SEQ ID NO: 2), VPDTG (SEQ ID NO: 41), IPQTG (SEQ ID NO: 42), YPRRG (SEQ ID NO: 43), LPMTG (SEQ ID NO: 44), LAFTG (SEQ ID NO: 45), LPQTS (SEQ ID NO: 46), LPXT, LAXT, LPXA, LGXT, IPXT, NPXT, NPQS (SEQ ID NO: 47), LPST (SEQ ID NO: 48), NSKT (SEQ ID NO: 49), NPQT (SEQ ID NO: 50), NAKT (SEQ ID NO: 51), LPIT (SEQ ID NO: 52), or LAET (SEQ ID NO: 53).

In some embodiments, a sortase substrate used in the labeling methods as described herein can further comprises one or more additional amino acids, e.g., at the N or C terminus of the sortase recognition sequence. For example, one or more amino acids (e.g., up to 5 amino acids) having the identity of amino acids found immediately N-terminal to, or C-terminal to, a five (5) amino acid recognition sequence in a naturally occurring sortase substrate may be incorporated. Such additional amino acids may provide context that improves the recognition of the recognition motif. In some examples, a sortase substrate may contain up to 50 amino acid residues, for example, up to 40, 30, 20, 15, 10, or 5 amino acid residues.

In some embodiments, the sortase recognition sequence in the sortase substrate can be masked. In contrast to an unmasked sortase recognition motif, which can be recognized by a sortase, a masked sortase recognition motif is a motif that is not recognized by a sortase but that can be readily modified ("unmasked") such that the resulting motif is recognized by the sortase. For example, in some embodiments, at least one amino acid of a masked sortase recognition motif comprises a side chain comprising a moiety that inhibits, e.g., prevents, recognition of the sequence by a sortase of interest, e.g., SrtAaureus. Removal of the inhibiting moiety, in turn, allows recognition of the motif by the sortase. Masking may, for example, reduce recognition by at least 80%, 90%, 95%, or more (e.g., to undetectable levels) in certain embodiments. By way of example, in certain embodiments a threonine residue in a sortase recognition motif such as LPXTG (SEQ ID NO: 1) may be phosphorylated, thereby rendering it refractory to recognition and cleavage by SrtA. The masked recognition sequence can be unmasked by treatment with a phosphatase, thus allowing it to be used in a SrtA-catalyzed transamidation reaction.

A sortase substrate used in the labeling methods described herein is conjugated to a detectable label. The term "conjugated" or "conjugation" refers to an association of two molecules, for example, two proteins or a protein and an agent, e.g., a small molecule, with one another in a way that they are linked by a direct or indirect covalent or non-covalent interaction. In certain embodiments, the association is covalent, and the entities are said to be "conjugated" to one another. In some embodiments, a protein is post-translationally conjugated to another molecule, for example, a second protein, a small molecule, a detectable label, a click chemistry handle, or a binding agent, by forming a covalent bond between the protein and the other molecule after the protein has been formed, and, in some embodiments, after the protein has been isolated. In some embodiments, two molecules are conjugated via a linker connecting both molecules. For example, in some embodiments where two proteins are conjugated to each other to form a protein fusion, the two proteins may be conjugated via a polypeptide linker, e.g., an amino acid sequence connecting the C-terminus of one protein to the N-terminus of the other protein. In some embodiments, two proteins are conjugated at their respective C-termini, generating a C—C conjugated chimeric protein. In some embodiments, two proteins are conjugated at their respective N-termini, generating an N—N conjugated chimeric protein. In some embodiments, conjugation of a protein to a peptide is achieved by transpeptidation using a sortase. See, e.g., Ploegh et al., WO/2010/087994, and Ploegh et al., WO/2011/133704, and Ploegh et al., International PCT Application PCT/US2014/037545, filed May 9, 2014, the entire contents of each of which are incorporated herein by reference, for exemplary sortases, proteins, recognition motifs, reagents, and methods for sortase-mediated transpeptidation.

A detectable label is a moiety that has at least one element, isotope, or functional group incorporated into the moiety which enables detection of the molecule, e.g., a protein or peptide, or other entity, to which the label is attached. Labels can be directly attached (i.e., via a bond) or can be attached by a linker (such as, for example, an optionally substituted alkylene; an optionally substituted alkenylene; an optionally substituted alkynylene; an optionally substituted heteroalkylene; an optionally substituted heteroalkenylene; an optionally substituted heteroalkynylene; an optionally substituted arylene; an optionally substituted heteroarylene; an optionally substituted acylene, or any combination thereof, which can make up a linker). It will be appreciated that the label may be attached to or incorporated into a molecule, for example, a protein, polypeptide, or other entity, at any position. In general, a detectable label can fall into any one (or more) of five classes: a) a label which contains isotopic moieties, which may be radioactive or heavy isotopes, including, but not limited to, $^{2}H$, $^{3}H$, $^{13}C$, $^{14}C$, $^{15}N$, $^{18}F$, $^{31}P$, $^{32}P$, $^{35}S$, $^{67}Ga$, $^{76}Br$, $^{99m}Tc$ (Tc-99m), $^{111}In$, $^{123}I$, $^{125}I$, $^{131}I$, $^{153}Gd$, $^{169}Yb$, and $^{186}Re$; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label fluorescein-isothiocyanate (FITC); d) a label which has one or more photo affinity moieties; and e) a label which is a ligand for one or more known binding partners (e.g., biotin-streptavidin, FK506-FKBP). In certain embodiments, a label comprises a radioactive isotope, preferably an isotope which emits detectable particles, such as particles. In certain embodiments, the label comprises a fluorescent moiety. In certain embodiments, the label is the fluorescent label fluorescein-isothiocyanate (FITC). In certain embodiments, the label comprises a ligand moiety with one or more known binding partners. In certain embodiments, the label comprises biotin. In some embodiments, a label is a fluorescent polypeptide (e.g., GFP or a derivative thereof such as enhanced GFP (EGFP)) or a luciferase (e.g., a firefly, *Renilla*, or *Gaussia luciferase*). It will be appreciated that, in certain embodiments, a label may react with a suitable substrate (e.g., a luciferin) to generate a detectable signal. Non-limiting examples of fluorescent proteins include GFP and derivatives thereof, proteins comprising fluorophores that emit light of different colors such as red, yellow, and cyan fluorescent proteins. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M. and Kain, S R (eds.) Green fluorescent protein: properties, applications, and protocols Methods of biochemical analysis, v. 47 Wiley-Interscience, Hoboken, N.J., 2006; and Chudakov, D M, et al., Physiol Rev. 90(3):1103-63, 2010, for discussion of GFP and numerous other fluorescent or luminescent proteins. In some embodiments, a label comprises a dark quencher, e.g., a substance that absorbs excitation energy from a fluorophore and dissipates the energy as heat.

Labeling of a cell expressing a sortase acceptor peptide fused to a member of a ligand-receptor pair can be detected via a routine method, depending upon the detectable label conjugated to the sortase substrate. For example, if a fluorescent dye or a label that releases a detectable signal is used, the labeled cells can be detected by, e.g., FACS analysis. In another example, the sortase substrate is conjugated to biotin and the cells can be further incubated with streptavidin and then analyzed by, e.g., FACS. When the fusion protein further comprises a protein tag, a labeled antibody specific to the protein tag can be used for detected labelled cells.

Cells that are labelled in the labelling methods described herein can be isolated and subject to further analysis, as described herein.

(iv) In Vivo Labeling

In other embodiments, the intercellular labeling methods described here may be performed in vivo, for, e.g., tracking cell-cell interactions in vivo. Such an in vivo assay can be performed in a suitable subject, for example, a non-human animal such as a non-human mammal (e.g., mouse, rat, rabbit, dog, cat, or monkey).

In some examples, the two engineered cells described herein, one expressing a sortase or an active fragment thereof on the surface and the other expressing a surface polypeptide comprising a sortase acceptor peptide at the N-terminus, can be prepared in vitro following routine technology or as described herein. Either or both of the sortase/active fragment and the sortase acceptor peptide may or may not be fused to a member of a receptor-ligand pair. Those engineered cells can then be transferred into a suitable subject via a suitable route, for example, intravenous infusion. The subject can be co-administered with a suitable labelled sortase substrate as described herein.

In other examples, one or both of the nucleic acids encoding a polypeptide comprising the sortase/active fragment and the nucleic acid encoding a polypeptide comprising the sortase acceptor peptide can be introduced into the genome of a suitable non-human animal (e.g., zebrafish or a non-human mammal, such as a mouse, a rat, a rabbit, or a monkey) to make a transgenic animal. Alternatively, one or both of the nucleic acids encoding the sortase and/or the sortase acceptor peptide can be inserted into the genome of a suitable non-human animal at the endogenous locus (loci) encoding one or both members of the ligand-receptor pair for producing one or both the fusion polypeptides in the transgenic animal. In this case, the endogenous gene encoding one or both members of the ligand-receptor pair is used for producing the fusion polypeptides.

A "transgenic animal" as used herein can be any animal containing one or more cells bearing genetic materials for expressing one or both of the fusion polypeptides described herein, directly or indirectly, by deliberate genetic manipulation at the subcellular level, such as by targeted recombination or microinjection or infection with recombinant virus. The term "transgenic animal" is meant to encompass animals in which one or more cells receive a recombinant DNA molecule as described herein. This molecule may be specifically targeted to a defined genetic locus, be randomly integrated within a chromosome, or it may be extra-chromosomally replicating DNA. Any of the transgenic animals, either engineered to express one fusion polypeptide or both fusion polypeptide as described herein, are within the scope of the present disclosure.

The transgenic animal described herein can be a non-human animal, e.g., a mammal such as a rodent (e.g., a rat or mouse), in which an exogenous nucleic acid encoding a fusion polypeptide as described herein is inserted into its genome, i.e., one or more of the cells of the animal includes a nucleic acid(s) encoding one or both of the fusion polypeptides described herein. In some examples, it may have the exogenous nucleic acid sequence present as an extrachromosomal element in a portion of its cell. In other examples, the exogenous nucleic acids can be stably integrated into its germ line DNA (i.e., in the genomic sequence of most or all of its cells). Other examples of transgenic animals include non-human primates, sheep, dogs, cows, goats, chickens, amphibians, etc. Unless otherwise indicated, it will be assumed that a transgenic animal comprises stable changes to the germline sequence. Exogenous nucleic acid is introduced into the germ line of such a transgenic animal by genetic manipulation of, for example, embryos or embryonic stem cells of the host animal.

A transgene comprising an exogenous nucleic acid of interest for use in constructing any of the transgenic animals described herein can be constructed via routine technology. A transgene is a nucleotide sequence that has been or is designed to be incorporated into a cell, particularly a mammalian cell, that in turn becomes or is incorporated into a living animal such that the nucleic acid containing the nucleotide sequence is expressed (i.e., the mammalian cell is transformed with the transgene). A transgene typically comprises the coding sequence for an exogenous protein of interest (here a fusion polypeptide as described herein) under the control of a regulatory sequences for a "characterizing gene." The regulatory sequence can be an endogenous promoter of a characterizing gene. This characterizing gene is endogenous to a host cell or host organism (or is an ortholog of an endogenous gene) and is expressed in a particular select population of cells of the organism (e.g., in immune cells such as T or B cells).

Methods for constructing transgenes are well known in the art, including, but not limited to, in vitro recombinant DNA techniques and in vivo genetic recombination. See, e.g., Sambrook et al., 2001, *Molecular Cloning, A Laboratory Manual*, Third Edition, Cold Spring Harbor Laboratory Press, N.Y.; and Ausubel et al., 1989, Current Protocols in Molecular Biology, Green Publishing Associates and Wiley Interscience, N.Y., both of which are hereby incorporated by reference in their entireties.

Introduction of a nucleic acid encoding an exogenous polypeptide (e.g., a transgene as described herein) can be achieved by a variety of methods including, for example, microinjection of half-day embryo pronuclei, transfection of embryonic stem cells, or fusion of embryonic stem cells with yeast spheroplasts or micronuclei comprising transchromosomes. The transgenic animal such as transgenic mammals (non-human) resulting from the processes described herein are capable of functionally rearranging the introduced exogenous genetic sequences, and expressing one or both of the fusion polypeptides as described herein. Transgenic nonhuman mammals such as rodents (e.g., mice) are particularly suitable for use in the methods described herein.

In some examples, the exogenous nucleic acids as described herein of may integrate into the genome of a suitable animal recipient (or an oocyte or embryo that gives rise to the recipient organism), e.g., by random integration or site-specific integratin. If random, the integration preferably does not knock out, e.g., insert into, an endogenous gene(s) such that the expression of the endogenous gene is not affected. Alternatively, the exogenous nucleic acid may integrate by a directed method, e.g., by directed homologous recombination ("knock-in"), Chappel, U.S. Pat. No. 5,272,071; and PCT publication No. WO 91/06667, published May 16, 1991; U.S. Pat. No. 5,464,764; Capecchi et al., issued Nov. 7, 1995; U.S. Pat. No. 5,627,059, Capecchi et al. issued, May 6, 1997; U.S. Pat. No. 5,487,992, Capecchi et al., issued Jan. 30, 1996). Preferably, when homologous recombination is used, it does not knock out or replace the host's endogenous copy of the characterizing gene.

Methods for generating cells having targeted gene modifications through homologous recombination are known in the art. The construct will comprise at least a portion of the characterizing gene with a desired genetic modification, e.g., insertion of the nucleotide sequence coding for the tagged ribosomal protein and will include regions of homology to the target locus, i.e., the endogenous copy of the characterizing gene in the host's genome. DNA constructs for random integration need not include regions of homology to mediate recombination. Markers can be included for performing positive and negative selection for insertion of the nucleic acid of the invention.

To create a homologous recombinant transgenic animal, a homologous recombination vector can be prepared, in which the exogenous nucleotide sequence encoding the fusion polypeptide is flanked at its 5' and 3' ends by characterizing gene sequences to allow for homologous recombination to occur between the exogenous gene carried by the vector and the endogenous characterizing gene in an embryonic stem cell of the animal. The additional flanking nucleic acid sequences are of sufficient length for successful homologous recombination with the endogenous characterizing gene. Typically, several kilobases of flanking DNA (both at the 5' and 3' ends) are included in the vector. Methods for constructing homologous recombination vectors and homologous recombinant animals are known in the art. See, e.g., Thomas and Capecchi, 1987, Cell 51: 503; Bradley, 1991, Curr. Opin. Bio/Technol. 2: 823-29; and PCT Publication Nos. WO 90/11354, WO 91/01140, WO 92/0968, and WO 93/04169.

Alternatively, a homologous recombination vector can be prepared, in which the exogenous nucleotide sequence encoding the sortase or the sortase acceptor peptide is flanked at its 5' and 3' ends by sequences homologous to the endogenous gene locus for a member of the ligand-receptor pair to allow for homologous recombination to occur between the exogenous gene carried by the vector and the endogenous gene locus in an embryonic stem cell of the animal. The homologous recombination is designed such that fusion polypeptide(s) comprising the sortase and one member of the ligand-receptor pair, the sortase acceptor peptide and the other member of the ligand-receptor pair, or both can be produced in the transgenic animal thus prepared. The additional flanking nucleic acid sequences are of sufficient length for successful homologous recombination with the endogenous characterizing gene. Nucleotide sequences encoding the sortase or the sortase acceptor peptide can also be inserted into the endogenous gene locus for one or both of the members of the ligand-receptor pair via site-specific recombination, e.g., via the Cre/LoxP system known in the art.

In one example, a transgenic animal of the present disclosure can be created by introducing one or more nucleic acids encoding one or both of the fusion polypeptide operably linked to suitable promoters into the male pronuclei of a fertilized oocyte, e.g., by microinjection or retroviral infection, and allowing the oocyte to develop in a pseudopregnant female foster animal. Methods for generating transgenic animals via embryo manipulation and microinjection, particularly animals such as mice, are well known in the art, see, e.g., U.S. Pat. Nos. 4,736,866 and 4,870,009, U.S. Pat. No. 4,873,191, Hogan, Manipulating the Mouse Embryo, (Cold Spring Harbor Laboratory Press, Cold Spring Harbor, N.Y., 1986) and Wakayama et al., 1999, Proc. Natl. Acad. Sci. USA, 96:14984-89. Similar methods are used for production of other transgenic animals.

In another embodiment, the exogenous nucleic acid as described herein can be inserted into the genome of an embryonic stem (ES) cell or an induced pluripotent stem cells (iPS) cell, followed by injection of the modified ES cell or iPS cell into a blastocyst-stage embryo that subsequently develops to maturity and serves as the founder animal for a line of transgenic animals.

For example, a vector comprising the exogenous nucleic acid can be introduced into ES cells (e.g., by electroporation) and cells in which the introduced gene has homologously recombined with the endogenous gene are selected. See, e.g., Li et al., 1992, Cell 69:915. For embryonic stem (ES) cells, an ES cell line may be employed, or embryonic cells may be obtained freshly from a host, e.g., mouse, rat, guinea pig, etc.

After transformation, ES cells can be grown on an appropriate feeder layer, e.g., a fibroblast-feeder layer, in an appropriate medium and in the presence of appropriate growth factors, such as leukemia inhibiting factory (LIF). Cells that contain the construct may be detected by employing a selective medium. Transformed ES cells may then be used to produce transgenic animals via embryo manipulation and blastocyst injection. (See, e.g., U.S. Pat. Nos. 5,387,742, 4,736,866 and 5,565,186 for methods of making transgenic animals.)

Stable expression of the construct is preferred. For example, ES cells that stably express a nucleotide sequence encoding a fusion polypeptide as described herein may be engineered. ES host cells can be transformed with DNA, e.g., a plasmid, controlled by appropriate expression control elements (e.g., promoter, enhancer, sequences, transcription terminators, polyadenylation sites, etc.), and a selectable marker. Following the introduction of the exogenous DNA, engineered ES cells may be allowed to grow for 1-2 days in an enriched media, and then are switched to a selective media. The selectable marker in the recombinant plasmid confers resistance to the selection and allows cells to stably integrate the plasmid into their chromosomes and expanded into cell lines.

The selected ES cells can then injected into a blastocyst of an animal (e.g., a mouse) to form aggregation chimeras. See, e.g., Bradley, 1987, in Teratocarcinomas and Embryonic Stem Cells: A Practical Approach, Robertson, ed., IRL, Oxford, 113-52. Blastocysts can be obtained from 4 to 6 week old superovulated females. The ES cells can be trypsinized, and the modified cells can be injected into the blastocoel of the blastocyst. After injection, the blastocysts can be implanted into the uterine horns of suitable pseudopregnant female foster animal. Alternatively, the ES cells may be incorporated into a morula to form a morula aggregate which is then implanted into a suitable pseudopregnant female foster animal. Females are then allowed to go to term and the resulting litters screened for mutant cells having the construct.

The chimeric animals can be screened for the presence of the modified gene. By providing for a different phenotype of the blastocyst and the ES cells, chimeric progeny can be readily detected. Males and female chimeras having the modification are mated to produce homozygous progeny. Only chimeras with transformed germline cells would generate homozygous progeny. If the gene alterations cause lethality at some point in development, tissues or organs can be maintained as allergenic or congenic grafts or transplants, or in in vitro culture.

Progeny harboring homologously recombined or integrated exogenous DNA in their germline cells can be used to breed animals in which all cells of the animal contain the homologously recombined DNA by germline transmission of the exogenous nucleic acid as described herein. Clones of the non-human transgenic animals described herein can also be produced according to the methods described in Wilmut et al., 1997, Nature 385: 810-13 and PCT Publication NOS. WO 97/07668 and WO 97/07669. Once the transgenic mice are generated, they may be bred and maintained using methods well known in the art. See, e.g., Manipulating the Mouse Embryo. A Laboratory Manual, 2nd edition. B. Hogan, Beddington, R., Costantini, F. and Lacy, E., eds. 1994. Cold Spring Harbor Laboratory Press: Plainview, N.Y.

A transgenic founder animal can be identified based upon the presence of the exogenous nucleic acid in its genome and/or expression of mRNA encoding the fusion polypeptide described herein in tissues or cells of the animals. A transgenic founder animal can then be used to breed additional animals carrying the exogenous nucleic acid as described herein. Moreover, transgenic animals carrying the exogenous nucleic acid can further be bred to other transgenic animals carrying other exogenous nucleic acids. For example, a transgenic animal carrying the exogenous nucleic acid encoding the fusion polypeptide comprising a sortase and one member of a ligand-receptor pair can be bred with another transgenic animal carrying the exogenous nucleic acid encoding the fusion polypeptide comprising a sortase acceptor peptide and the other member of the ligand-receptor pair to produce a double knock-in transgenic animal.

In some embodiments, genome editing technology (also known as genome editing with engineered nucleases or GEEN) may be used to modify endogenous genes of interest for making the transgenic animals as described herein. Gene editing is a type of genetic engineering, in which DNA is inserted, replaced, or removed from a genome using artificially engineered nucleases, e.g., Zinc finger nucleases (ZFNs), Transcription Activator-Like Effector Nucleases (TALENs), the CRISPR/Cas system, and engineered meganuclease re-engineered homing endonucleases. See, e.g., Esvelt, et al., (2013), Mol Syst Biol 9 (1): 641; Tan et al., (2012), Adv Genet 80: 37-97; and Puchta et al., (2013), Int. J. Dev. Biol 57: 629-637. Any of such genome editing technology can be used for preparing the transgenic animals described herein.

In other embodiments, a transgenic animal such as transgenic mouse capable of expressing one fusion polypeptide as described herein can be constructed following the methods described herein. Such a transgenic animal can then be administered with engineered cells expressing the other fusion polypeptide via routine methods. For example, a transgenic animal capable of expressing a fusion polypeptide comprising a sortase and one member of a ligand-receptor pair can be administered with engineered cells expressing a fusion polypeptide comprising a sortase acceptor peptide fused to the other member of the ligand-receptor pair, or vice versa.

An animal or subject that express both fusion polypeptides as described herein can then be administered with a labeled sortase substrate as described herein. In some examples, the labeled sortase substrate and engineered cells expressing one or both fusion polypeptides are co-administered into a subject or transgenic animal.

The term "co-administration" is meant to refer to a combined administration by a suitable route(s), in which two or more agents are administered to a subject. The agents may be in the same dosage formulations or separate formulations. For combined administration with more than one agent, where the agents are in separate dosage formulations, the agents can be administered concurrently, or they each can be administered at separately staggered times. The agents may be administered simultaneously or sequentially (e.g., one agent may directly follow administration of the other or the agents may be give episodically, e.g., one can be given at one time followed by the other at a later time, e.g., within a week), as long as they are given in a manner sufficient to allow both agents to achieve effective concentrations in the body. The agents may also be administered by different routes, e.g., one agent may be administered intravenously while a second agent is administered intramuscularly or orally. Thus, the engineered cells may be administered prior to, concomitant with, or after the administration of the labelled sortase substrate. Co-administrable agents also may be formulated as an admixture, as, for example, in a single formulation. These formulations may be parenteral or oral, such as the formulations described, e.g., in U.S. Pat. Nos. 6,277,384; 6,261,599; 5,958,452 and PCT publication No. WO 98/25613, each hereby incorporated by reference.

Afterwards, cells expressing the fusion polypeptide comprising the sortase acceptor peptide and one member of the ligand-receptor pair can be either detected in vivo, e.g., by imaging, or isolated from the subject and subjected to further analysis in vitro (e.g., by FACS analysis).

II. Kits

Some aspects of the present disclosure provide kits useful for performing the intercellular labeling methods described herein, which is catalyzed by a sortase and mediated by ligand-receptor interaction. Such a kit can comprise (a) a first cell expressing a first polypeptide that comprise a sortase acceptor peptide as described herein, which is located at the N-terminus of the first polypeptide, and (b) a second cell expressing a second polypeptide that comprise a suitable sortase or an active fragment thereof. In some embodiments, the first polypeptide further comprises a member of a receptor-ligand pair, such as those described herein, and the second polypeptide further comprises the other member of the receptor-ligand pair. In other embodiments, the first polypeptide and one member of the receptor-ligand pair are expressed on the first cell as separate polypeptides. The second polypeptide and the other member of the receptor-ligand pair can also be expressed on the surface of the second cell as separate polypeptide.

The kit may further comprise any of the labeled sortase substrate described herein. The sortase can transfer a suitable sortase substrate as described herein onto the acceptor peptide. In some embodiments such a kit may comprise one or more nucleic acids that encode the first or second polypeptide, e.g., nucleic acids that can be inserted into a vector or used directly to generate cells that express the first or second polypeptide.

In some embodiments, the kit may comprise (i) a plurality of antigen-presenting cells (APCs), such as B cells, macrophages, or DCs; (ii) a T cell; and optionally (iii) a labeled sortase substrate. The APCs express one or both of MHC Class I and MHC Class II complexes. Further, the APC s express a polypeptide comprising a sortase acceptor peptide, which is located at the N-terminus of the polypeptide. Collectively, the plurality of APCs also express polypeptides encoded by a cDNA library. The T cell in the kit expresses a T cell receptor, which may be endogenous or exogenous. Such a T cell also express a polypeptide comprising a sortase such as SrtA or an active fragment thereof. Such a kit can be used to identify the cognate antigen of a T cell receptor with unknown specificity.

Alternatively or in addition, the kits described herein can comprise one or more of the medium components for use in in vitro culturing of the cells described herein, e.g., one or more growth factors and nutritional factors for cell growth. If immune cells are involved, the medium components might include suitable cytokines needed for maintenance and growth of the immune cells.

Further, the kit can comprise a suitable sortase substrate which is conjugated to a detectable label as described herein. The selection of the suitable sortase substrate would depend on the sortase used in the kit. See above discussions.

In some embodiments, the kit further comprises a buffer or reagent useful for carrying out a sortase-mediated transpeptidation reaction.

III. Application of the Intercellular Labelling Methods

The intercellular labeling method described herein provides a solution for tracking molecule interactions, particularly in vivo, which has not been achieved in the art. This method may be used for various purposes, including, but not limited to, identifying agents capable of modulating the interaction between a specific receptor and its cognate ligand, identifying B cells expressing high affinity B-cell receptors (thus high affinity antibodies) by tracking interaction between B cells and follicular T helper cells in germinal centers, or identifying a binding partner of a protein of interest.

(i) Screening for Agents Capable of Modulating Ligand-Receptor Interaction

To screen for potential modulators of a ligand-receptor pair (e.g., inhibitors or enhancers), a candidate agent can be co-cultured with the pair of cells described herein, one expressing a polypeptide which comprises a sortase or an active fragment thereof and one member of a receptor-ligand pair, and the other cell expressing a polypeptide comprising a corresponding sortase acceptor peptide and the other member of the ligand-receptor pair in the presence of a suitable labeled sortase substrate, which comprises a sequence that is recognizable by the just-noted sortase. In some instances, the polypeptide comprising a sortase or the active fragment thereof and the member of a receptor-ligand pair are expressed as separate polypeptides on the cell surface. In other instances, they are expressed as one fusion polypeptide. Alternatively or in addition, the sortase acceptor peptide and the other member of the receptor-ligand pair may be expressed as separate polypeptides on cell surface or expressed as one fusion polypeptide.

The labeling level of the cell expressing the fusion polypeptide comprising the sortase acceptor peptide is measured in the presence and absence of the candidate agent. If the level of labeling changes in the presence of the candidate agent as relative to in the absence of the candidate agent, it indicates that the candidate agent is a potential modulator of the involved ligand-receptor pair. For example, if the level of labeling increases in the presence of the candidate agent, such an agent might enhance the interaction between the ligand and receptor. On the other hand, if the level of labeling decreases in the presence of the candidate agent, such an agent might inhibit the interaction between the ligand and receptor.

(ii) Identifying B Cells Expressing High Affinity B Cell Receptors

One of the key characteristics of the immune system is the ability to react to pathogens by generating soluble molecules called antibodies or immunoglobulins (Igs). An effective immune response requires the production of antibodies that bind antigen with high affinity and specificity.

The immune system can generate antibodies capable of recognizing a virtually unlimited number of antigenic determinants. This requires enormous variability among Igs. The first process accounting for this variability is VDJ recombination. VDJ recombination takes place in the bone marrow before antigen exposure. There, B cells undergo combinatorial rearrangement of V, D and J gene segments, which encode for the antigen-binding portion of the Ig molecule. This mechanism provides a first source of variability which, although broad, is still limited when compared to the vast number of antigens potentially recognized by antibodies. Therefore, the first antibodies produced against an immunizing antigen are usually of low affinity.

Exposure to antigen triggers the generation and clonal selection of B cells carrying novel mutant Ig sequences with improved antigen affinity, in a phenomenon known as affinity maturation. Affinity maturation is the result of the combination of two processes: somatic hypermutation and affinity-based selection, both of which occur in anatomic structures referred to as germinal centers (GCs). These structures arise in secondary lymphoid organs, such as the spleen and lymph nodes, about one week after primary antigen exposure. GCs are composed of two functionally distinct compartments: the light zone (LZ) and the dark zone (DZ). B cell proliferation is restricted to the DZ. Also in the DZ, insertion of somatic genetic mutations into Ig variable regions ensures further expansion of Ig variability. Affinity-based selection of Igs after somatic hypermutation occurs in the LZ. Recent studies pinpointed the LZ decision-making process to the antigen-dependent interaction between GC B cells and follicular T helper (Tfh) cells, which are the limiting factor in affinity-based selection of GC B cells. According to the proposed model, B cells that exhibit high affinity Ig molecules at the plasma membrane will capture and process more antigen for presentation on Major Histocompatibility Complex (MHC) class II molecules. A limiting number of Tfh cells then selects those B cells with the highest peptide-MHC density and directs their return to the DZ, where they undergo rapid division. By contrast, B cells that fail to interact with Tfh cells undergo apoptosis.

Despite the crucial role of the interaction between Tfh cells and B cells in affinity maturation, little is known about how these interactions lead to selection of some cells and elimination of others in vivo. This gap is due largely to the fact that there is no effective way to determine the extent to which two cells have interacted within a living animal.

The intercellular labeling approach described herein would allow for measuring interactions between immune cells in vivo during a GC reaction. Such a system could be used to distinguish between B cells based on the intensity of their interactions with other Tfh cells, and would therefore provide a powerful tool to investigate Tfh-mediated selection of GC B cells in a physiological setting and to identify B cells expressing high affinity BCRs to antigens (thus high affinity antibodies). The labeling intensity is expected to correlate with BCR affinity. The method can also be used to determine the ligand-receptor interaction(s) that is important in in vivo selection of B cells expressing high affinity BCRs.

As used herein, a B cell receptor or BCR refers to a transmembrane receptor protein located on the outer surface of B-cells, comprising a membrane-bound antibody that, like all antibodies, has a unique and randomly determined antigen-binding site. A BCR is composed of two parts: (i) a membrane-bound immunoglobulin molecule of one isotype (IgG, IgD, IgM, IgA or IgE); and (ii) a signal transduction moiety, which is an Igα/Igβ heterodimer (CD79). Each member of the dimer spans the plasma membrane and has a cytoplasmic tail bearing an immunoreceptor tyrosine-based activation motif (ITAM).

As used herein, "binding affinity" refers to the apparent association constant or KA. The KA is the reciprocal of the dissociation constant (KD). The BCRs or antibodies isolated from the methods described herein may have a binding affinity (KD) of at least $10^{-5}$, $10^{-6}$, $10^{-7}$, $10^{-8}$, $10^{-9}$, $10^{-10}$ M, or lower. An increased binding affinity corresponds to a decreased KD. Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding antigen as a function of target antigen concentration. The concentration of bound binding antigen ([Bound]) is related to the concentration of free target antigen ([Free]) and the concentration of binding sites for the binding antigen on the target where (N) is the number of binding sites per target molecule by the following equation:

[Bound]=[N][Free]/(Kd+[Free])

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

To perform the method for identifying B cells expressing high affinity BCRs from, e.g., a germinal center, a non-human mammal (e.g., mouse, rat, rabbit, or monkey) may be provided, which carries (i) B cells (e.g., naive B cells) expressing a B cell receptor and surface polypeptide comprising a sortase acceptor peptide located at the N-terminus of the polypeptide, and (ii) a different type of immune cells such as T cells that express a surface polypeptide comprising a sortase. The immune cells such as T cells may also display a ligand that is recognizable by the BCR. In some embodiments the surface polypeptide comprising a sortase acceptor peptide and the surface polypeptide comprising a sortase can be fused to members of a ligand-receptor pair (e.g., any of the ligand-receptor pairs described herein).

The non-human mammal can be administered with a labeled sortase substrate, which comprises a sortase recognition sequence. Any of the sortase, sortase acceptor peptides, and sortase substrates that comprise sortase recognition sequences described herein can be used in this method. Selection of a suitable combination of the sortase, sortase acceptor peptide, and sortase substrate is also described herein. The labeled sortase substrate delivered into the mammal would bind to the immune cells such as T cells that express a surface fusion polypeptide comprising a sortase. Upon interaction between the B cell and the immune cell (e.g., T cell) via BCR/ligand binding, the sortase catalyzes a transpeptidation reaction to transfer the labelled sortase substrate onto the sortase acceptor peptide on B cells. Lymphocytes can then be isolated from a suitable tissue, such as a germinal center or lymph node and labeled B cells can be purified for further analysis. Such labeled B cells express high affinity BCRs (and thus high affinity antibodies) to antigens.

In some embodiments, the non-human mammal may be immunized with an antigen of interest following routine practice. Exemplary antigens include, but are not limited to, proteins or other biological molecules expressed by a pathogen (e.g., a bacterial pathogen or a viral pathogen) or the pathogen itself, optionally inactivated or attenuated, tumor antigens or tumor cells or oncogenic proteins. The resulting antibody may in some embodiments be used as a therapeutic agent, e.g., to target a pathogen or tumor.

Immunization of a host animal with a target antigen or a fragment containing the target antigen conjugated to a protein that is immunogenic in the species to be immunized, e.g., keyhole limpet hemocyanin, serum albumin, bovine thyroglobulin, or soybean trypsin inhibitor using, for example, a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or $R^1N=C=NR$, where R and $R^1$ are different alkyl groups), can yield a population of antibodies (e.g., polyclonal antibodies). Labeled B cells isolated from such a non-human mammal may be subjected to further screening to identify those that express high affinity BCRs specific to the antigen of interest.

The isolated labeled B cells can be cultured in vitro following routine methods. Nucleic acids encoding the heavy chain, the light chain, or both, or a portion thereof (e.g., a fragment comprising at least one complementarity determining region such as the variable regions of heavy and light chains) of the BCR can be isolated from the labeled B cells. The nucleic acids may be subjected to further sequencing to determine the coding sequences. In some examples, a nucleic acid(s) encoding at least the CDR3 of the heavy chain, the CDR3 of the light chain, or both can be isolated and sequenced. In other examples, a nucleic acid(s) encoding all of the CDR1-CDR3 of the heavy chain, all of the CDR1-CDR3 of the light chain, or both can be isolated and sequenced. In yet other examples, a nucleic acid(s) encoding the whole variable region of the heavy chain, the whole variable region of the light chain, or both are isolated and sequenced. If the CDRs are derived from a non-human mammal, such CDRs can be grafted into a suitable human heavy chain or light chain framework to produce humanized antibodies. Alternatively or in addition, specificity determining residues (SDRs) may be identified, which may be grafted into a human heavy chain and/or light chain framework. Methods for isolating nucleic acids encoding a BCR heavy and/or light chain gene, or a portion thereof as described herein are well known in the art. See, e.g., Mockridge et al., Clinical and Experimental Immunology, 114:129-136 (1998).

The nucleic acids thus isolated can be cloned into a suitable expression vector for producing high affinity antibodies. The expression vector may be introduced into a host cell, e.g., a mammalian host cell, such as a Chinese hamster ovary (CHO) cell, an NS0 murine myeloma cell, a PER.C6® human cell, etc., which may be used to produce the antibodies.

Alternatively, the isolated labeled B cells can be used to produce hybridoma cell lines using the conventional hybridoma technology. For example, hybridomas can be prepared from the labeled B cells and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce monoclonal high affinity antibodies, e.g., antibodies specific to the protein of interest. The hybridomas can be expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal high affinity antibodies. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen.

The non-human mammal as described herein may be established by transferring the B cells and a different type of immune cells (e.g., T cells), which can be constructed in vitro, into a host non-human mammal via a suitable route (e.g., intravenous infusion) as described herein. Alternatively, the non-human mammal may be a transgenic mammal engineered for producing (a) B cells expressing a surface polypeptide comprising a sortase acceptor peptide and a B cell receptor, (b) a different type of immune cells such as T cells that express a surface polypeptide comprising a sortase or an active fragment thereof, or both (a) and (b). In one example, the non-human mammal is a double knock-in transgenic mammal that produces both (a) and (b). In another example, the non-human mammal is a single knock-in transgenic mammal that produces one of (a) and (b) and is transferred with the other via, e.g., infusion. Any of the transgenic mammals described herein can be prepared by a method known in the art and/or those described herein. See above descriptions.

In some embodiments, the non-human mammal is a humanized mammal such as a humanized mouse or humanized rat engineered for producing fully human antibodies or a fragment thereof such as human-mouse or human-rat chimeric antibodies. Such a humanized mammal may have one or more human immunoglobulin loci, or a portion thereof, inserted into the corresponding mouse or rat endogenous immunoglobulin loci. Alternatively, such a humanized mammal may carry one of more human immunoglobulin genes, which may be inserted into one chromosome the mammal or remain as extrachromosomal genetic material. Humanized mice expressing human antibodies are known in the art, including the VelocImmune mice provided by Regeneron Pharmaceuticals, Inc., Kymouse™ mice provided by Kymab, XenoMouse™ provided by Abgenix, and HuMAb mice provided by Medarex/GenPharm). Methods for preparing transgenic mice capable of producing human antibodies are known in the art. See, e.g., U.S. Pat. Nos. 5,591,669, 5,598,369, 5,545,806, 5,545,807, and 6,150,584, the relevant disclosures thereof are incorporated by reference herein. Alternatively, such a humanized mammal may be naturally deficient in its own immune system or have had its own immune system ablated and have reconstituted with the human immune system or human hematopoietic stem cells to produce human immune cells. Examples include SCID mice, NOG mice, or NSG mice.

In some embodiments the intercellular labeling approach described herein may be used for measuring interactions between immune cells in vitro, e.g., for purposes of identifying B cells that express a BCR with high affinity for an antigen of interest. For example, a population of B cells expressing different BCRs (e.g., a library of B cells engineered to express different BCRs or isolated from a subject) and a sortase acceptor peptide such as G5 at the cell surface may be mixed with a population of $CD4^+$ T cells and a soluble antigen of interest. The $CD4^+$ T cells express a sortase or an active fragment thereof at their cell surface. The sortase may be expressed as part of a fusion protein with a cell surface receptor or ligand (which may be one that is upregulated upon a cognate interaction) or may be otherwise fused to a transmembrane domain or membrane anchoring domain that tethers the sortase to the cell membrane and allows it to be exposed to the external environment. B cells that express a BCR with high affinity for the antigen will take up more of the antigen than B cells that express a lower affinity BCR and will present it more highly (e.g., in the form of peptides bound to cell surface MHC), causing interaction with $CD4^+$ T cells that express a TCR that is specific for the antigen. The mixture of B cells and CD4+ T cells is contacted with a labeled sortase substrate, and the B cells that interact with the $CD4^+$ T cells become labeled. Such B cells can then be isolated (e.g., by FACS) and nucleic acid (e.g., DNA) encoding the BCR may be isolated, thereby identifying the BCR, as described above.

(iii) Identifying Binding Partners of a Protein of Interest

The intercellular labeling methods described can also be used for identifying binding partners of a protein of interest. For example, one or more nucleotide sequences coding for a polypeptide comprising a sortase as described herein and a protein of interest (e.g., a cell surface receptor such as a receptor of an immune cell) can be introduced into a first cell. The nucleotide sequences encoding the polypeptide comprising the sortase and the protein of interest may be linked for producing a fusion polypeptide or separated for expressing individual polypeptides. Further, a plurality of genes encoding a plurality of polypeptide binding candidates, and a nucleotide sequence encoding a polypeptide comprising a sortase acceptor peptide at the N-terminus can be introduced into a population of cells. The sortase acceptor peptide may or may not fused to the polypeptide binding candidates. The plurality of polypeptide binding candidates encompass potential binding partners for the protein of interest. When needed, each of the plurality of polypeptides may further comprise a protein tag, which may facilitate protein detection and purification.

The first cell and the population of cells can be incubated in the presence of a suitable sortase substrate, which is associated with a detectable label under conditions allowing for occurrence of the transpeptidation reaction catalyzed by the sortase to conjugate the labeled sortase substrate to the sortase acceptor peptide. Cells conjugated to the detectable label can then be isolated via a routine method, e.g., by cell sorting. The labeled cells thus identified can be further analyzed to determine the polypeptide expressed on those cells, which can be are binding partners for the protein of interest. The binding activities of the thus identified polypeptides can be confirmed by a conventional binding assay, e.g., ELISA assay.

Any of the sortases, sortase substrates (which comprise a sortase recognition sequence), and sortase acceptor peptides described herein can be in this screening method. Selection of suitable combinations of the three components are also disclosed herein or known to those skilled in the art.

(iv) Identifying Antigen Specificity of T Cells

The intercellular labeling methods described herein may also be useful to identify the cognate antigen of a T cell with unknown specificity. An intercellular labeling system comprising the following components may be used to achieve this aim: (a) a plurality of antigen presenting cells engineered to express a surface polypeptide that comprises an N-terminal sortase acceptor peptide (e.g., those described herein such as an oligoglycine fragment, e.g., G5 fragment; SEQ ID NO: 3); (b) a T cell engineered to express a surface polypeptide comprising a sortase or an active fragment thereof such as those described herein (e.g., SrtA); and (c) a substrate of the sortase that contains a sortase recognition sequence and is conjugated to a label, e.g., biotin, a fluorophore, or other detectable label such as those described herein.

In some instances, the sortase, the sortase acceptor peptide, or both can be fused with a cell surface protein that is upregulated upon a cognate interaction. In some embodiments, the sortase expressed by the T cell and the sortase acceptor peptide expressed by the APC s are not fused to members of the same ligand-receptor pair. For example, the sortase and the sortase acceptor peptide may be fused to receptors or ligands that are not members of the same receptor-ligand pair (e.g., PDGFR/CD40, PDGFR/CD86) or fused to any polypeptides that comprise a transmembrane domain or membrane anchor domain such that the sortase and the sortase acceptor peptide are expressed at the cell surface and exposed to the extracellular environment. In some embodiments, either or both the sortase and the sortase acceptor peptide are fused to a transmembrane domain of a receptor or ligand that is/are upregulated upon a cognate interaction. In some embodiments the sortase or the sortase acceptor peptide, but not both, is fused to a transmembrane domain of a receptor or ligand that is upregulated upon cognate interaction.

The plurality of APCs can be any type of cells capable of presenting antigens to T cells. Examples include, but are not limited to, B cells DCs, or macrophages. Each of the APCs expresses a MHC Class I molecule, a MHC Class II molecule, or both, which may be of any suitable origin (e.g., human, murine or any other species of interest). In one example, the MHC Class I and/or MHC Class II is endogenous. In another example, one or more exogenous genes encoding the MHC Class I and/or MHC Class II molecules are introduced into host APCs to produce the APCs for use in the method described herein. When the T cell used in this method is obtained from a subject, at least one of the MHC Class I and/or MHC Class II molecules expressed on the APCs may match one HLA allele of that subject.

The plurality of the APCs described herein also express, collectively, polypeptides encoded by a cDNA library. The cDNA library can be constructed from any source of interest, e.g., human, murine, or any other species of interest.

In some embodiments the cDNA library may be constructed from cancer cells or cancer tissue. In some embodiments, cancer cells or tissue may be obtained from a biopsy or surgery or isolated from a blood sample. The cancer cells or cancer may be of any type (e.g., any of the various types mentioned herein). Cancer cells may overexpress certain proteins that might be absent or expressed only at low levels in normal cells and/or may express mutant proteins that might not be present in normal cells. Such proteins may, for example, serve as cancer antigens. In some embodiments it is of interest to identify those antigens, e.g., particular antigens that are recognized by T cells and/or B cells and may not be expressed by normal cells or may be expressed at a much lower level by normal cells. In some embodiments, such identification may be useful in the context of personalized medicine, e.g., generating vaccines or cell therapies tailored for a particular cancer patient.

In some embodiments the cDNA library may be constructed from cells or tissues of a particular type, e.g., cells or tissues that are subject to immune-mediated attack in an autoimmune disease. This may be useful, e.g., to identify particular antigens against which the immune system mounts an attack in autoimmune disease.

The T cell used in the method described herein expresses a T cell receptor (TCR) whose antigen specificity needs to be determined. In one example, the TCR is endogenous. In another example, one or more exogenous genes encoding a TCR complex can be introduced into a host T cell, which may have the endogenous TCR gene deleted or inactivated. The T cell may be derived from a cancer patient, e.g., from a site where tumor grows. Such a T cell may target a cancer antigen. Alternatively, the T cell may be derived from a site where infection occurs. Such a T cell may target an antigen of a pathogen, e.g., a viral antigen or a bacterial antigen. In other instances, the T cell may be derived from a site affected by an autoimmune disease, e.g., synovial fluid, pancreatic lymph node, or cerebral spinal fluid. Such T cells may be autoreactive T cells targeting autoantigens.

To perform the method described herein, the plurality of APCs may be brought into contact with the T cell in the presence of the labeled sortase substrate. The contacting step may be performed in vitro by, e.g., co-culturing the APC cells and the T cell in the presence of a labeled sortase substrate as described herein. Alternatively, the contacting step may be performed in vivo, for example, the APC cells, the T cell, and the labeled sortase substrate can be delivered into a suitable host (e.g., mouse or rat) via a suitable route (e.g., intravenous or subcutaneous injection). If an APC cell displays a peptide/MHC complex that can interact with the TCR on the T cell, the spatial proximity would allow the sortase expressed on the T cell to transfer the labeled sortase substrate onto the sortase acceptor peptide on the APC cell, thereby labeling the APC cell.

In some embodiments the T cell may be of a particular T cell subset, e.g., cytotoxic T cells (e.g., CD8$^+$ T cells), helper T cells (e.g., CD4$^+$ T cells), or a subset thereof.

The labeled APCs may be recovered by a suitable method such as FACS sorting. When needed, the population of labeled APCs may be enriched before sorting by, e.g., immune-magnetic isolation, using specific reagents recognizing the label attached to the substrate (e.g., biotin, or fluorophores). Such reagents may be commercially available. After sorting, the cDNA sequence carried by the labeled APC can be recovered via conventional technology, e.g., PCR amplification followed by sequencing analysis. The results obtained from the analysis would reveal the antigen specificity of the TCR of interest, which is encoded by a member of the cDNA library expressed in the T cell.

Once identified, the antigen could be produced (e.g., using standard protein expression methods). The antigen, optionally combined with an adjuvant, may be administered to a subject in need thereof (e.g., as a prophylactic or therapeutic vaccine).

In some embodiments APCs, e.g., DCs, are contacted with the antigen ex vivo (allowing them to take up and process the antigen) or are engineered to express the antigen, and then administered to a patient. The APCs may then interact with T cells in the patient to stimulate the immune response. In some embodiments APCs, e.g., DCs, are contacted with the antigen ex vivo (allowing them to take up and process the antigen) or are engineered to express the antigen and then contacted with T cells ex vivo. The T cells are subsequently administered to the patient). In some embodiments, the T cells are autologous. In some embodiments, the T cells may be expanded ex vivo prior to contacting them with APCs or afterwards.

Another application of the technology for identifying antigens that are recognized by T cells may be in the context of immune responses against transplanted organs, cells, or tissues. One could isolate T cells that have infiltrated into organs or tissues that may be subject to autoimmune attack or rejection and identify the antigen(s) recognized by such T cells.

In some embodiments, in the case of antigens that are recognized by T cells in subjects suffering from an autoimmune disease or rejection of transplanted organ, tissue, or cells, the identified antigen may be used to induce tolerance to the antigen or used in other strategies to reduce or prevent an immune response against the antigen and thereby reduce an autoimmune response or immune response against a transplanted organ, tissue, or cells. Such strategies might include administering antibodies, peptides or small molecules that block interaction between the TCR and the antigen or specifically deplete T cells that recognize the antigen.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Intercellular Labeling Mediated by CD40/CD40L Interaction

To track intercellular interactions between ligand and receptor molecules expressed at the plasma membrane of cells, ligand and receptor pairs were engineered by genetic fusion so that one of the interacting partner expressed S. aureus SortaseA (SrtA) enzyme at its extracellular portion and the other one presented 5 extracellular N-terminal glycine residues (FIG. 1A). A triple mutated version of SrtA enzyme (P94S-D160N-K196T) with improved catalytic properties as described by Chen et al. PNAS, 2011 (FIG. 1B) was employed. Upon ligand-receptor interaction, and in presence of a biotinylatated or fluorescently labeled SrtA substrate as the short peptide LPETG (SEQ ID NO: 2), spatial proximity allows the labeled substrate to be transferred from the SrtA-engineered ligand to the N-terminus glycine of the receptor.

Figure 2:
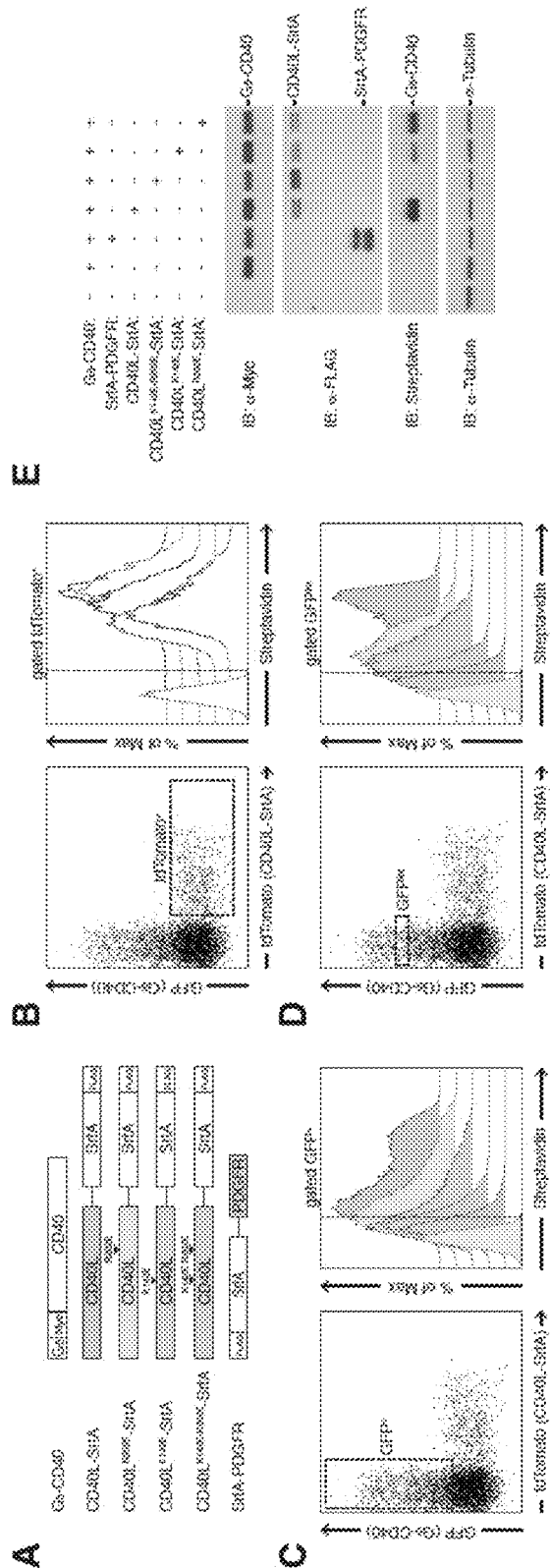
FIG. 2. Intercellular labeling mediated by CD40/CD40L interaction. (A) A schematic representation of the constructs employed in this experiment. (B) Graphs showing expression of SrtA-fusion constructs in HEK293T. HEK293T cells were transfected with the constructs listed in (A). Cells carrying G5-CD40 construct (GFP reporter vector) were incubated with cells transfected with different SrtA-fusion constructs (tdTomato reporter vector), treated with biotinylated SrtA substrate, stained with streptavidin, and analyzed by flow cytometry. Dot plot of a representative sample shows tdTomato$^+$ gating. Histogram plot shows binding of SrtA substrate to SrtA-fusion construct transfected cells (constructs are color-coded as in panel A; grey peak corresponds to untransfected cells). (C-D) Intercellular labeling mediated by CD40/CD40L interaction in HEK293T cells. Cells were transfected and treated as in (B). Dot plot of a representative sample shows GFP$^+$ (C) or GFP$^{int}$ (D) gating. Histogram plots shows labeling of gated G5-CD40$^+$ cells by the different SrtA-fusion construct transfected cells. (E) G$_5$-CD40 specificity of intercellular labeling mediated by CD40/CD40L interaction. HEK293T cells were transfected with the constructs listed in (A). Cells carrying G$_5$-CD40 construct were incubated with cells transfected with different SrtA-fusion constructs, treated with biotinylated SrtA substrate, and analyzed by western blot with streptavidin or antibodies specific for Myc tag (G$_5$-CD40 construct), FLAG tag (SrtA-fusion constructs) and α-tubulin.

Briefly, expression vectors carrying $G_5$-myc-CD40 and CD40L-SrtA fusion proteins as shown in FIG. 2A were constructed via routine recombinant technology. These expression vectors were transfected into HEK293T cells. After transfection, cells expressing $G_5$-myc-CD40 fusion proteins were incubated with cells expressing CD40L-SrtA fusion protein, SrtA-PDGFR fusion protein (a not-interacting partner as a negative control), or untransfected cells, for 30 min in presence of biotin-LPETGG (SEQ ID NO: 5) peptide. In the case of CD40-CD40L pair, additional controls were investigated, including three mutated version of CD40L-SrtA (CD40L$R_{202}$E-SrtA, CD40L$K_{142}$E-SrtA, and CD40L$K_{142}$E/$R_{202}$W-SrtA). These mutants are impaired in CD40 binding.

The cells were then washed, stained with Streptavidin and analyzed by flow cytometry. For all the tested ligand-receptor pairs, a strong labeling of $G_5$-expressing cells was observed when incubated with the matching interacting partner (e.g., $G_5$-myc-CD40 and CD40L-SrtA). FIGS. 2B, 2C, and 2D. The level of $G_5$-expressing cell labeling was much higher when incubated with cells expressing the wild-type CD40L-SrtA, as compared to that when incubated with cells expressing one of three mutants. FIGS. 2B, 2C, and 2D. When incubated with the non-interacting molecule SrtA-PDGFR, only a very limited degree of labeling was observed, indicating that ligand-receptor binding/affinity are required for efficient transfer of the labeled SrtA substrate. FIGS. 2B, 2C, and 2D.

In the case of CD40-CD40L pair, it was demonstrated by western blot analysis of the samples that the transfer of the labeled substrate occurs specifically on the $G_5$-CD40 molecule (FIG. 2E) as indicated by the presence in the Streptavidin detection of a defined band at the molecular weight corresponding to $G_5$-CD40.

Figure 3:
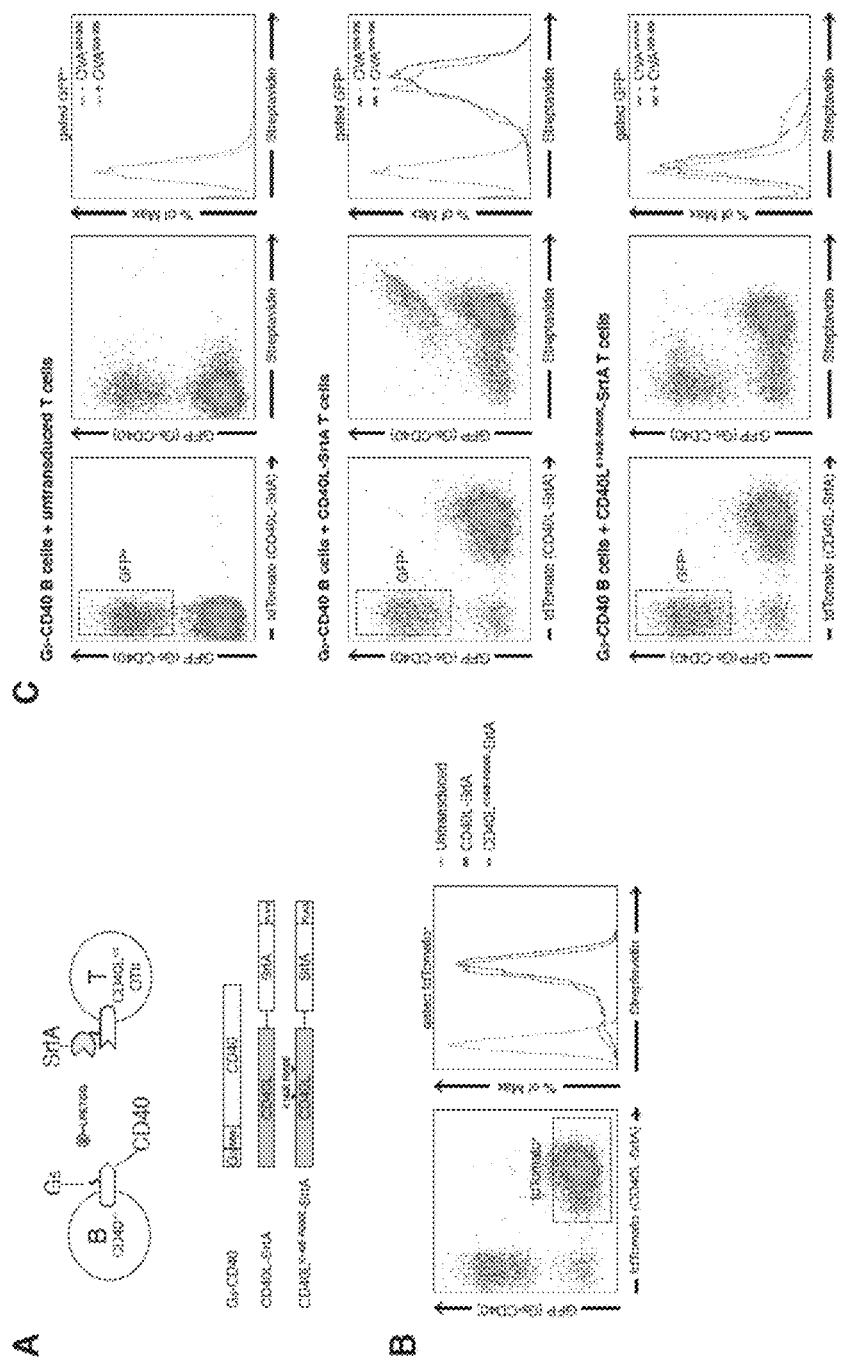
FIG. 3. Intercellular labeling in primary murine lymphocytes. (A) A schematic representation of the cells and constructs employed in this experiment. Primary murine B and CD4$^+$ T lymphocytes were purified from C57BL/6 CD40$^{-/-}$ mice and CD40L$^{-/Y}$ TCR-transgenic OT-II mice, respectively. CD4$^+$ T cells were transduced with retroviral vectors carrying CD40L-SrtA, CD40L$^{K142E-R202E}$-SrtA (both tdTomato reporter vector) or left untransduced. B cells were transduced with G5-CD40 (GFP reporter vector). (B) Expression of SrtA constructs in CD0$^+$ T cells. B and CD4$^+$ T lymphocytes were co-cultured in the presence or absence of OVA$^{323\text{-}339}$ peptide, treated with biotin-LPETGG (SEQ ID NO: 5) and stained with streptavidin before flow cytometry analysis. Dot plot shows gating of tdTomato$^+$ cells while histogram plot show binding of biotinylated substrate on gated SrtA expressing cells. (C) Intercellular labeling of G$_5$-CD40 B cells. Cells co-cultured and treated as in (B) were gated based on GFP expression to identify B cells carrying G5-CD40 construct (left dot-plot). Intensity of labeling in GFP$^+$ gated cells co-cultured with or without OVA$^{323\text{-}339}$ peptide is displayed on histogram plot.

Intercellular labeling between engineered CD40-CD40L pair was also tested in primary murine B and T lymphocytes (FIG. 3A). As observed in HEK293T cells, intercellular labeling of $G_5$-CD40 expressing B cells occurs efficiently upon interaction with CD4$^+$ T cells transduced with CD40L-SrtA, but it is present at a very low level when CD40L$K_{142}$E/$R_{202}$W-SrtA was used. FIGS. 3B and 3C. This result confirms that intercellular labeling in the system described herein reflects ligand-receptor interaction and/or affinity.

Example 2: Intercellular Labeling Mediated by Various Ligand-Receptor Pair Interaction Intercellular labeling mediated by additional ligand-receptor pair interaction (including CD28/CD80, CTLA4/CD80, CD28/CD86, CTLA4/CD86, PD-1/PD-L1, PD-1/PD-L2, and ICOS/ICOSL) was examined following the method described in Example 1 above.

Figure 4:
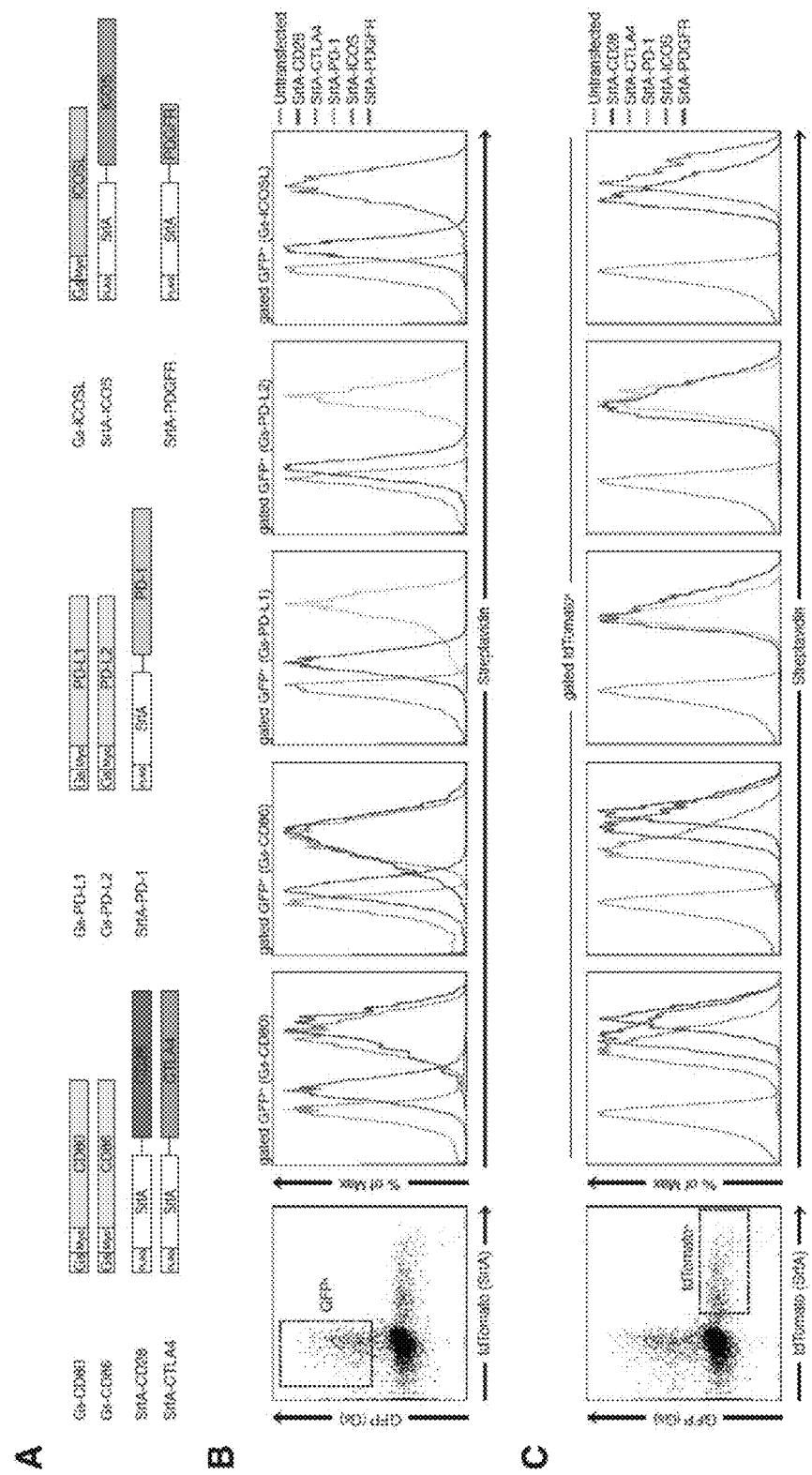
FIG. 4. Intercellular labeling mediated by various ligand-receptor pair interaction. (A) A schematic representation of the constructs employed in this experiment. (B) Cells carrying G$_5$-fusion constructs (GFP reporter vector) were incubated with cells transfected with different SrtA-fusion constructs (tdTomato reporter vector), treated with biotinylated SrtA substrate, stained with streptavidin and analyzed by flow cytometry. Each G$_5$-fusion construct (G$_5$-CD80, G$_5$-CD86, G$_5$-PD-L1, G$_5$-PD-L2, G$_5$-ICOSL) has been matched with the interacting partner(s), SrtA-PDGFR or untransfected cells. Dot plot of a representative sample shows GFP+ gating. Histogram plots shows labeling of gated G-fusion construct cells by different SrtA-fusion construct transfected cells. (C) Expression of SrtA-fusion constructs in HEK293T. Cells as in (B) were gated for tdTomato expression as in the dot plot to identify SrtA-expressing cells. Histogram plot shows binding of SrtA substrate to SrtA-fusion constructs.

Constructs for expressing the ligand/receptor fusion proteins are illustrated in FIG. 4A. These expression vectors were transfected into HEK293T cells. Cells expressing $G_5$-containing fusion proteins were included with cells expressing the corresponding interaction partner-Srt fusion proteins min in presence of a biotin-LPETGG (SEQ ID NO: 5) peptide. The cells were then washed, stained with Streptavidin and analyzed by flow cytometry. As shown in FIGS. 4B and 4C. A strong labeling of $G_5$-expressing cells was observed when incubated with cells expressing the interacting partner. These results further demonstrate that the cell labelled was mediated by receptor-ligand interaction.

Example 3: Intercellular Labeling in Primary Murine Lymphocytes

Figure 7:
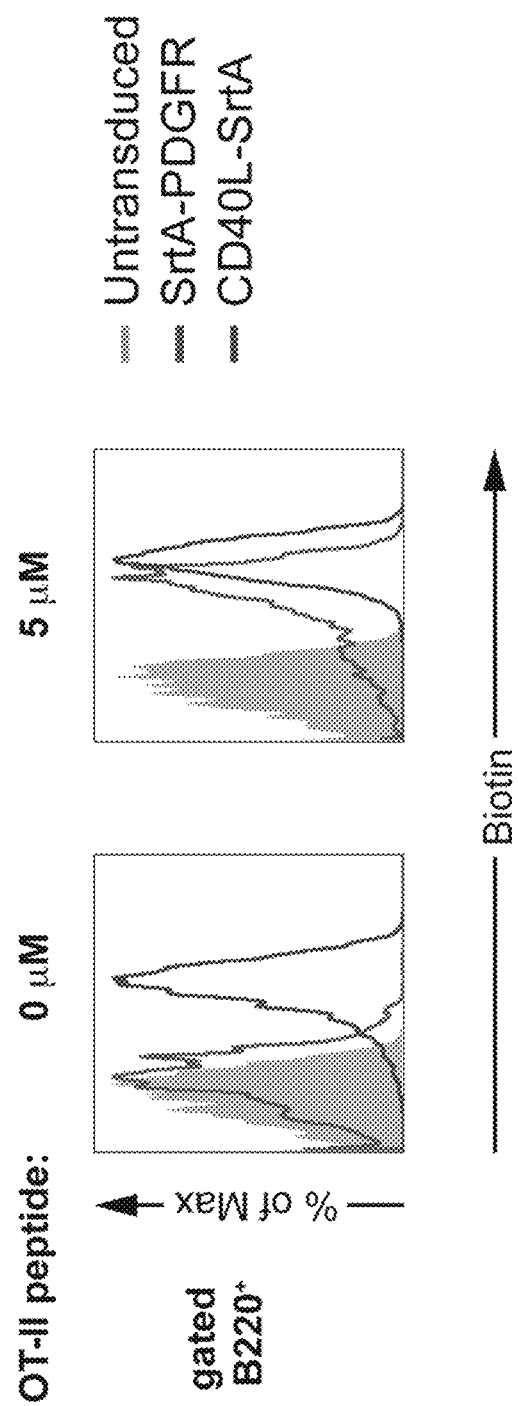
FIG. 7. Intercellular labeling in primary murine lymphocytes. Primary murine B and CD4+T lymphocytes were purified from C57BL/6 mice and TCR-transgenic OT-II mice, respectively. CD4+ T cells were transduced with retroviral vectors carrying CD40L-SrtA or SrtA-PDGFR or left untransduced. B cells were transduced with G5-CD40. B and CD4+T lymphocytes were co-cultured in presence or absence of OVA323-339 peptide, treated with biotin-LPETGG (SEQ ID NO: 5) and stained with streptavidin before flow cytometry analysis. Histogram plots show labeling of G5-CD40 B cells.

Intercellular labeling was also tested in primary murine B and T lymphocytes overexpressing SrtA/G5 tagged constructs (FIG. 7). As observed in HEK293T cells, intercellular labeling of $G_5$-CD40 expressing B cells occurs efficiently upon interaction with $CD4^+$ T OT-II cells overexpressing CD40L-SrtA, but it is present at a very low level when SrtA-PDGFR is used. When OT-II peptide is added to the co-culture, intercellular labeling is efficiently achieved with both CD40L-SrtA and SrtA-PDGFR expressing CD4+ T cells, indicating that cognate interaction can be tracked also using non interacting molecules (i.e., SrtA-PDFGR).

Example 4: Intercellular Labeling of Ligand-Receptor Interactions In Vivo

Figure 5:
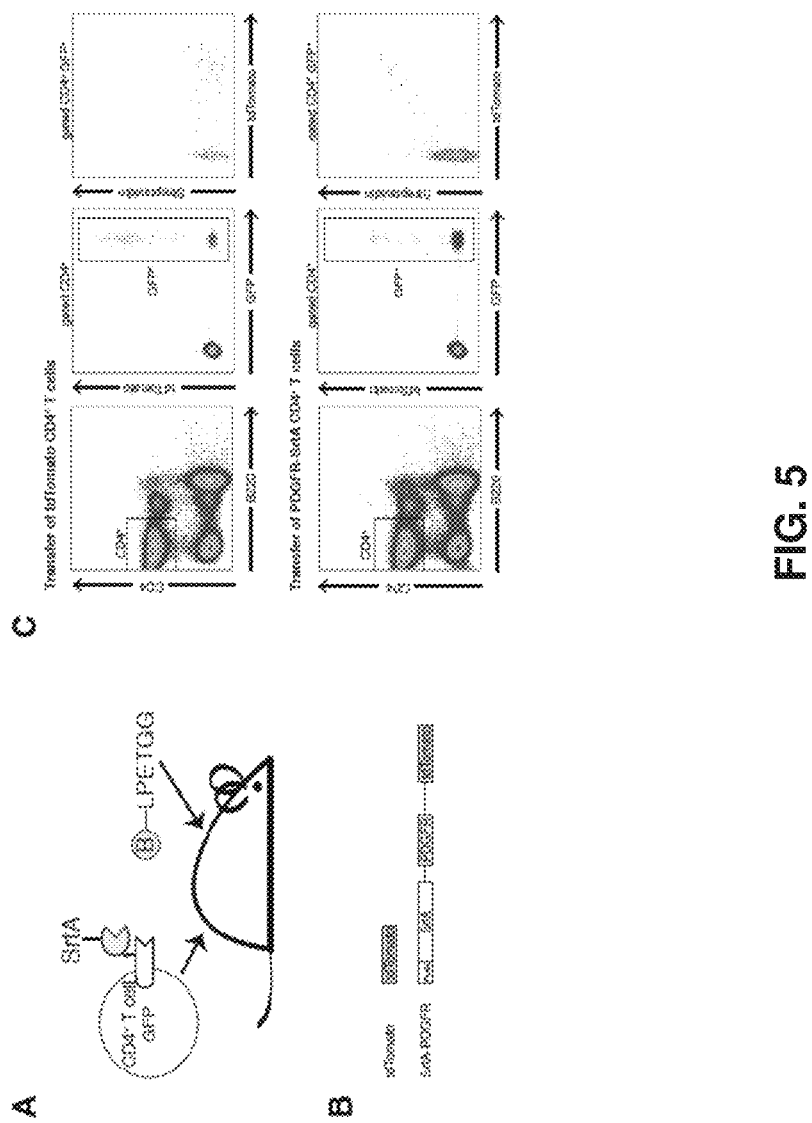
FIG. 5. Delivery of SrtA substrate and T cell labeling in vivo. (A) A schematic representation of the experimental setup. CD4$^+$ T cells were purified from C57BL/6 GFP$^+$ mice and transduced with either SrtA-PDGFR (tdTomato reporter vector) or tdTomato only as a control. 1.5×10$^6$ transduced CD4$^+$ T cells were transferred intravenously in recipient C57BL/6 and 250 nmol of biotin-LPETGG (SEQ ID NO: 5) injected subcutaneously at the base of the tail 24 hours after T cell transfer. Inguinal lymph nodes were harvested 1 hour after biotin-LPETGG (SEQ ID NO: 5) injection and analyzed by flow cytometry. (B) A schematic representation of the construct used in this experiment. (C) In vivo labeling of SrtA-expressing T cells. Dot plots show subsequent CD4$^+$ and GFP$^+$ gating to identify transferred CD4$^+$ T cells. Labeling intensity versus tdTomato expression is shown in dot plots on the right.

Interactions between different ligand-receptor pairs expressed by various subsets of immune cells are key events in the immune response but the tracking of these interactions in the context of a living animal has never been achieved. To test the application of the method described herein to follow ligand-receptor interactions in vivo, SrtA-PDGFR transduced T cells were transferred to a recipient mouse. 24 hours after the cell transfer, the mouse was also injected with biotin-LPETGG (SEQ ID NO: 5) peptide subcutaneously. Inguinal and popliteal lymph nodes were harvested 1 hour after substrate injection and analyzed by flow cytometry (FIG. 5).

SrtA transduced T cells shown a clear Streptavidin staining (SrtA forms a covalent intermediate with biotin-LPETGG (SEQ ID NO: 5)), indicating that SrtA substrate used readily distributed in the analyzed lymph nodes and that enzymatic activity is maintained in the extracellular milieu of the living animal.

Figure 6:
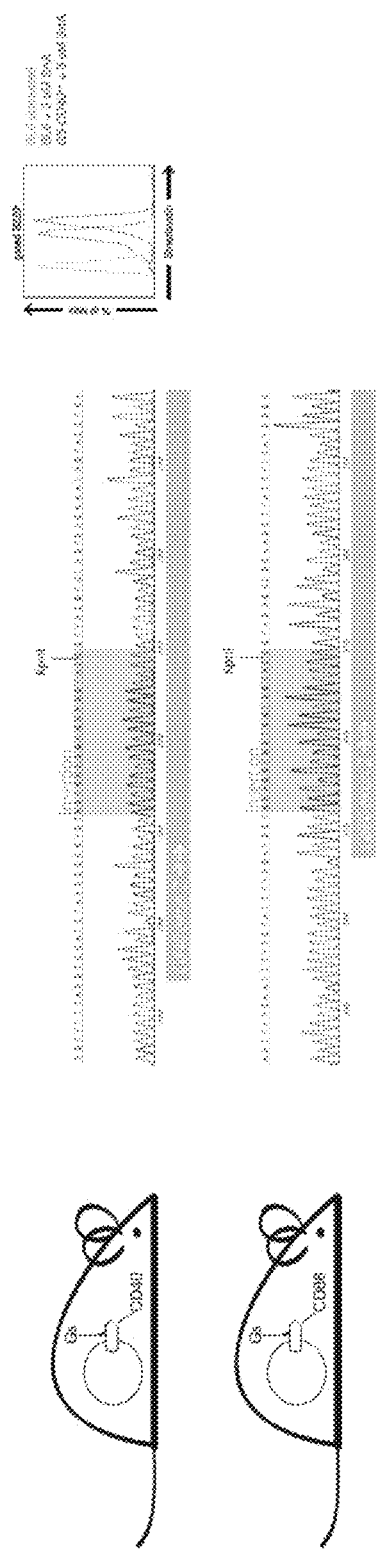
FIG. 6. G$_5$-CD40 or G$_5$-CD86 knock-in mice and labeling of cells expressing G$_5$-CD40 in the knock-in mice treated with a biotinylated SrtA substrate and SrtA. Left panel: a schematic illustration of the knock-in mice. Middle panel: a diagram showing sequencing results that confirm insertion of transgenes. Right panel: a diagram showing the labeling of lymphocytes isolated from G$_5$-CD40 knock-in mice treated with biotinylated SrtA substrate and 3 µM SrtA. Sequences, from top to bottom, correspond to SEQ ID NOs.: 56 and 57.

$G_5$-CD40 and $G_5$-CD86 knock-in transgenic mice were constructed. FIG. 6, left panel. The insertion of transgenes were confirmed by sequencing analysis. FIG. 6, middle panel. The mice were administered with biotin-LPETGG (SEQ ID NO: 5) and 3 µM SrtA. Lymphocytes were isolated from the treated mice, stained with streptavidin, and subjected to FACS analysis. As shown in FIG. 6, right panel, lymphocytes isolated from the $G_5$-CD40 knock-in mice were labeled, while lymphocytes isolated from control mice treated with 3 µM SrtA or untreated were not labeled.

Figure 8:
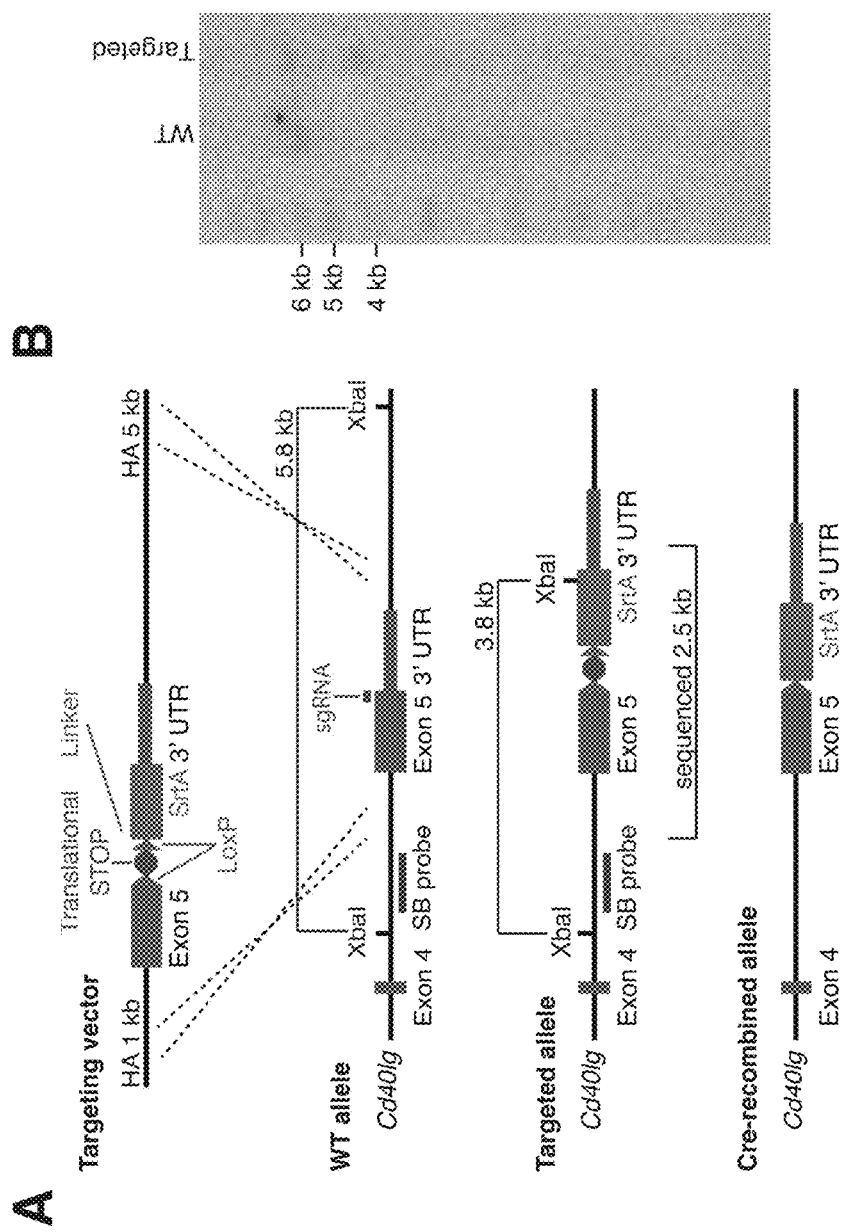
FIG. 8. Generation of CD40L-SrtA gene-targeted mouse. (A) Targeting strategy. (B) Southern blot analysis of CD40L-SrtA targeted mouse.
Figure 9:
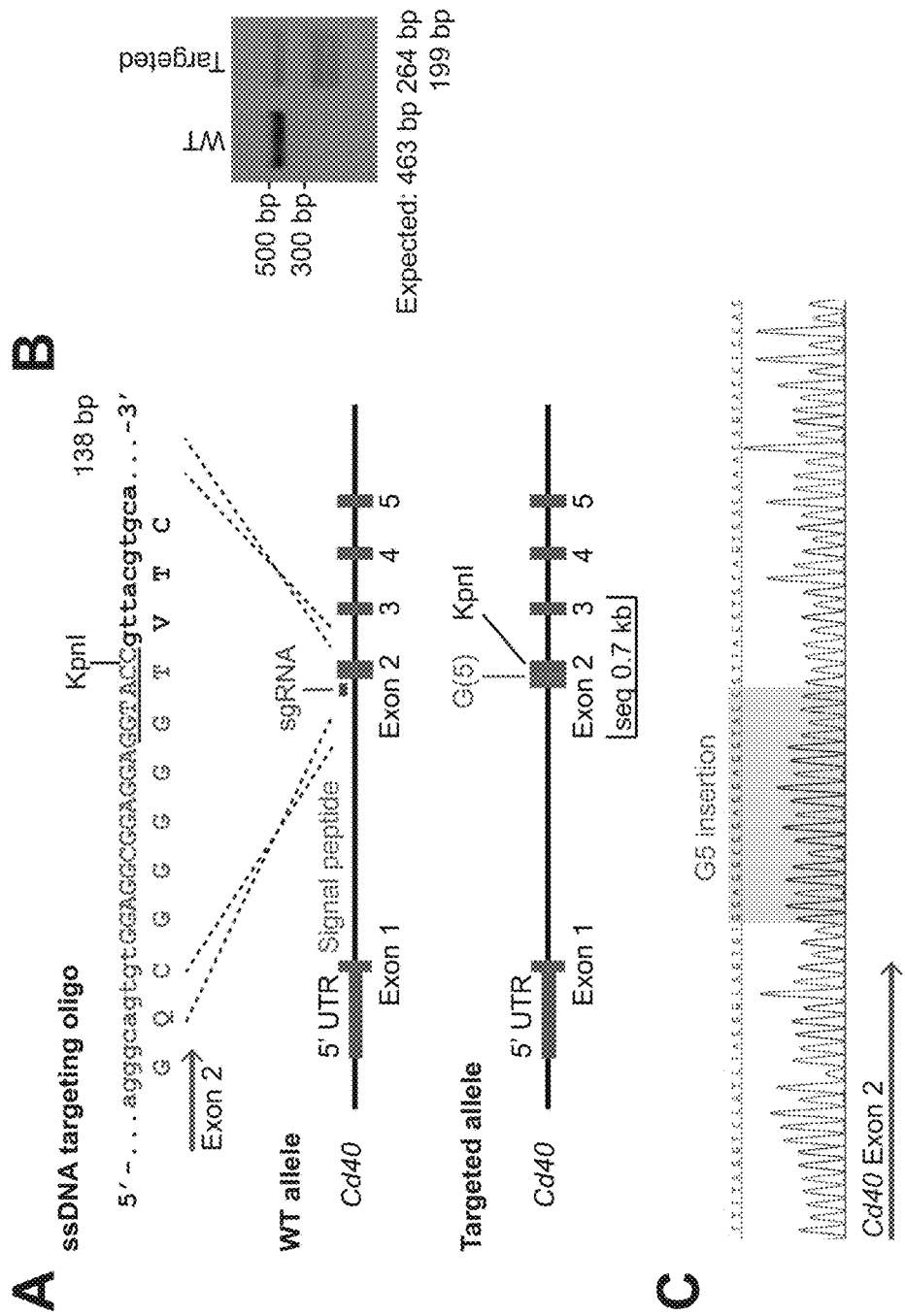
FIG. 9. Generation of G5-CD40 gene-targeted mouse. (A) Targeting strategy. Sequences from top to bottom correspond to SEQ ID NOs.: 58 and 59. (B) Restriction fragment length polymorphism analysis of targeted animal. (C) Sequencing results of the insertion region in the targeted animal. Sequence corresponds to SEQ ID NO: 60.

Further, two gene-targeted mice shown below were generated to test the labeling strategy described above to track cell:cell interactions in living animals:

(i) CD40L-SrtA mouse, carrying SrtA gene downstream the last coding exon of Cd40l gene (FIG. 8); and (ii) G5-CD40 mouse, carrying the genetic sequence encoding five glycine residues inserted in the second exon of Cd40 gene. (FIG. 9).

The labeling strategy in lymphocytes harvested from the two generated G5-CD40 and CD40L-SrtA mice noted above was investigated. B and CD4+T lymphocytes were harvested from G5-CD40+/+ and CD40L-SrtA+/Y OT-II mice, respectively, and cells were co-cultured for 16 hours in presence or absence of OVA223-239 peptide. Before flow cytometry analysis, cells were incubated for 1 additional hour with 100 uM Biotin-LPETGG (SEQ ID NO: 5). In this experiment antigen-dependent labeling of B cells was observed. Indeed, in absence of OVA223-239 peptide and so in absence of pMHC-II:TCR cognate interaction and consequent TCR triggering, CD40L-SrtA in CD4+ T cells was not found to express at the cell surface. In presence of OVA223-239 peptide, CD40L-SrtA was observed to be delivered at the plasma membrane in an OVA223-239 peptide-dose-depended manner. Once at the cell surface, CD40L was free to interact with CD40 molecules expressed constitutively by B cells and mediate intercellular labeling.

Example 5: Application of SrtA/G5 Intercellular Labeling Strategy in Antigen Discovery The SrtA/G5 intercellular labeling system was explored for its application in identifying cognate antigens for T cell receptors with unknown specificities.

Figure 10:
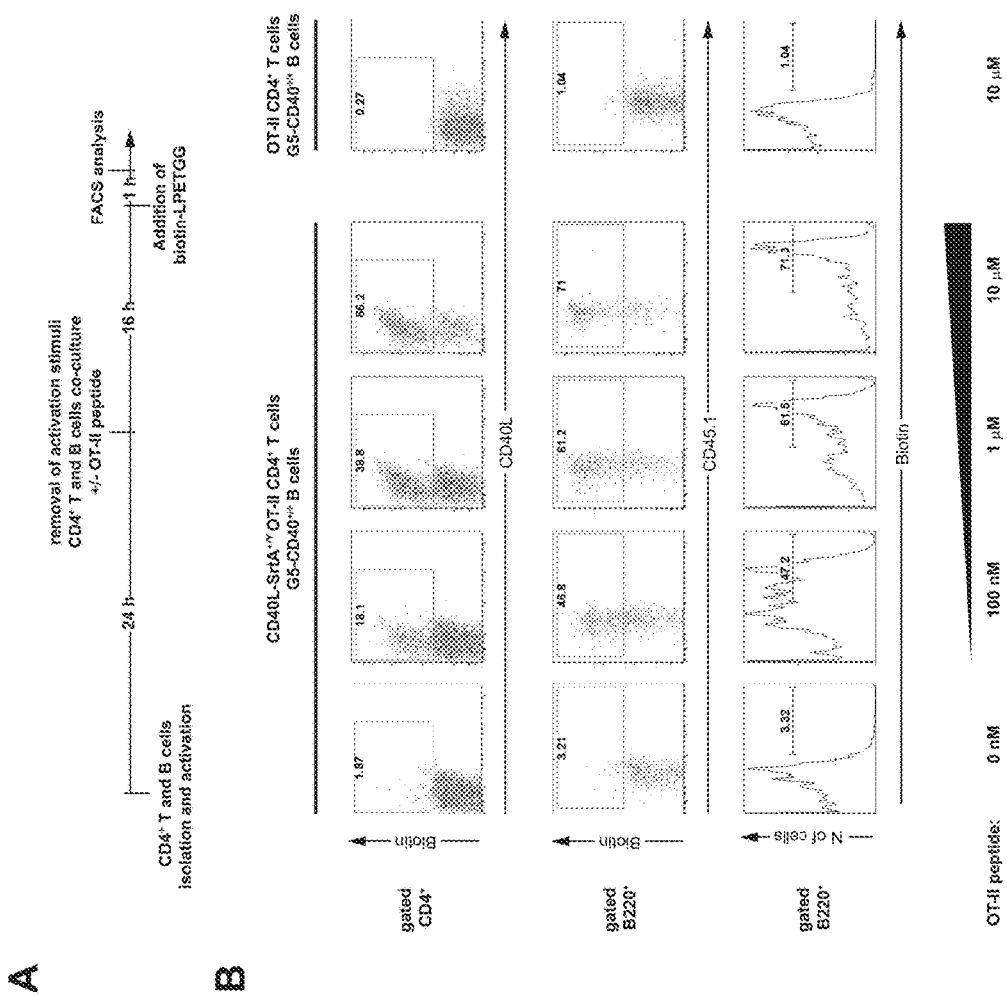
FIG. 10. Intercellular labeling upon B cell: CD4+ T cell interaction ex vivo. (A) Schematic representation of the experimental set-up. (B) Formation of Biotin-LPET:SrtA (SEQ ID NO: 54) covalent intermediate in CD40L-SrtA+/Y OT-II CD4+ T cells upon interaction with antigen-presenting B cells and dot-plot and histogram plot of G5-CD40+/+ B cells.

A schematic representation of the experimental set-up for studying intercellular labeling upon B cell:$CD4^+$ T cell interaction ex vivo is provided in FIG. 10, panel A. Briefly, CD40L-SrtA+/OT-II CD4+ T cells and G5-CD40+/+ B cells were isolated and activated. After removal of the activation stimuli, the CD4+ T cells and B cells were co-cultured for a suitable period. Biotin-LPETGG (SEQ ID NO: 5) was then added to the co-culture and the cells were subject to FACS analysis to examine biotin labeling of both the T cells and the B cells. FIG. 10, panel B.

Figure 11:
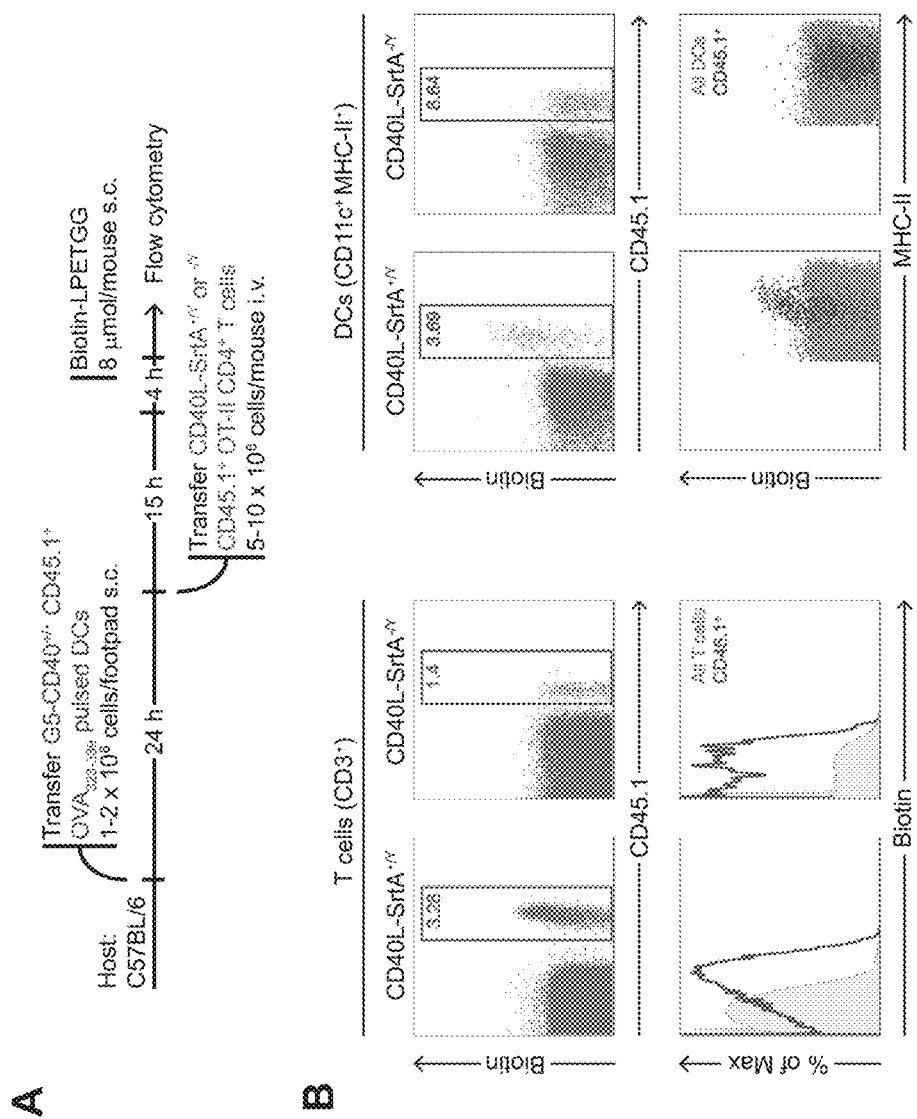
FIG. 11. Intercellular labeling upon DC:CD4+ T cell interaction in vivo. (A) Schematic representation of the experimental set-up. C57BL/6 mice were injected subcutaneously (s.c.) in the footpad with 1-2×106 OVA323-339 pulsed DCs/footpad. 24 hours later, mice were injected intravenously (i.v.) with 5-10×106 CD40L-SrtA+/Y or −/Y OT-II CD4+ T cells. 15 hours after T cell transfer, mice were injected s.c. with 1 umol of Biotin-LPETGG (SEQ ID NO: 5) every 30 min for a total of 4 hours. Popliteal LNs were then harvested and analyzed by flow cytometry. (B) Formation of Biotin-LPET:SrtA (SEQ ID NO: 54) covalent intermediate in CD40L-SrtA+/Y OT-II CD4+ T cells. (C) Labeling in the DCs population. Labeling is specifically detectable in antigen-pulsed DCs.

Further, intercellular labeling upon interaction of antigen-presenting cells (APCs) such as dendritic cells (DC) and T cells in vivo was investigated as follows. A schematic representation of the experimental set-up is provided in FIG. 11, panel A. G5-CD40$^{+/+}$ CD45.1$^+$ DCs were pulsed with OVA$_{323-339}$ and injected subcutaneously in the footpad of C57BL/6 mice (1-2×10$^6$ DCs per footpad). 24 hours later, the mice were further administered intravenously (i.v.) with 5-10×10 6 CD40L-SrtA$^{+/Y}$ or $^{-/Y}$ OT-II CD4$^+$ T cells. 15 hours after T cell transfer, the mice were injected subcutaneously (s.c.) with 1 µmol of biotin-LPETGG (SEQ ID NO: 5) every 30 min for a total of 4 hours. Popliteal lymphocytes (LNs) were then harvested and analyzed by flow cytometry. As shown in FIG. 11, panel B, formation of biotin-LPET:SrtA covalent intermediate in CD40L-Srt$^{+/Y}$ OT-II CD4$^+$ T cells was observed (left panel) and labeling was specifically detected in antigen-pulsed DCs (right panel).

The experiments presented above show how SrtA/G5 engineered surface molecules can be used to track intercellular interactions in vivo in mice. Using engineered G5-CD40 and CD40L-SrtA molecules, labeling of B cells and DCs by CD4$^+$ T cells upon cognate interaction, i.e., upon specific pMHC-II:TCR recognition, were achieved. Accordingly, this method can be used to discover cognate antigen recognized by TCRs whose specificity is unknown.

An exemplary system composed of the following components may be used to achieve this aim:

1. A collection of cell lines (human, murine or from any other species of interest) derived from antigen presenting cells (APCs; B cells, DCs, macrophages) engineered to express:
   MHC-I and MHC-II alleles (human, murine or from any other species of interest);
   a protein at the plasma membrane carrying N-terminal glycine residue(s); and
   a library of cDNAs (human, murine or from any other species of interest).
2. A T cell line engineered to express:
   a TCR whose specificity need to be determined
   a membrane protein carrying in its extracellular portion SrtA enzyme
3. A substrate for SrtA enzyme containing the amino acid sequence LPXTG (SEQ ID NO: 1) conjugated with biotin, a fluorophore or other detectable label.

Different SrtA/G5 pairs could be used to achieve labeling of APCs upon pMHC:TCR recognition. One strategy is to functionalize with SrtA/G5 ligand-receptor pairs which are upregulated upon pMHC:TCR recognition, as in the case of CD40-CD40L. Alternatively, labeling upon pMHC:TCR recognition can be achieved using a membrane bound form of SrtA (e.g., SrtA fused to PDGFR transmembrane domain) in combination with a G5 tagged protein that is upregulated upon cognate interaction (i.e., CD40, CD80, CD86).

In the assay, engineered APCs and T cells can be co-cultured in vitro in presence of a labeled SrtA substrate. Upon cognate interaction (specific pMHC:TCR recognition) between APCs and T cells intercellular labeling occurs and a subpopulation of APCs are labeled. These cells can be recovered by FACS sorting. If necessary, it is possible to enrich the population of labeled APCs before sorting using commercially available immuno-magnetic isolation, using specific reagents recognizing biotin or fluorophores. After sorting, exogenous DNA sequence can be identified by, e.g., PCR amplification and sequencing, revealing in this way the antigen specificity of the TCR of interest.

Antigens identified by the methods described herein as recognizable by T cells of interest, for example, T cell isolated from a tumor site or infectious site, may be useful as vaccine antigens for treating the corresponding cancer or infection.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. An intercellular labeling method comprising:
   (i) providing a first cell expressing a first polypeptide on the surface of the first cell, the first polypeptide comprising a sortase acceptor peptide, which is located at the N-terminus of the first polypeptide;
   (ii) providing a second cell expressing a second polypeptide on the surface of the second cell, the second polypeptide comprising a sortase or an active fragment thereof; and
   (iii) contacting the first cell with the second cell in the presence of a sortase substrate comprising a sortase recognition sequence, wherein the sortase substrate is associated with a detectable label;
   wherein upon interaction between the first cell and the second cell, the sortase or the active fragment thereof links the sortase substrate to the first polypeptide, thereby labeling the first cell expressing the first polypeptide, and wherein the first polypeptide the second polypeptide, or both, are fusion polypeptides.

2. The intercellular labeling method of claim 1, wherein the first polypeptide is a fusion polypeptide comprising the sortase acceptor peptide and one member of a receptor-ligand pair; and wherein the second polypeptide is a fusion polypeptide comprising the sortase or the active fragment thereof and the other member of the receptor-ligand pair.

3. The intercellular labeling method of claim 1, wherein the first cell, the second cell, or both are immune cells.

4. The intercellular labeling method of claim 3, wherein the first cell, the second cell, or both are T cells, B cells, dendritic cells, macrophages, or natural killer cells.

5. The intercellular labeling method of claim 2, wherein the receptor-ligand pair is selected from the group consisting of:
   CD40 and CD40L,
   CD80 and CD28,
   CD80 and CTLA4,
   CD86 and CD28,
   CD86 and CTLA4
   PD-1 and PD-L1,
   PD-1 and PD-L2, and
   ICOS and ICOSL.

6. The intercellular labeling method of claim 1, wherein the detectable label is biotin or a fluorescent dye.

7. The intercellular labeling method of claim 1, wherein the sortase is a sortase A.

8. The intercellular labeling method of claim 7, wherein the sortase is a mutant sortase A that comprises one or more mutations of P94R or P94S, S102C, A104H, E105D, K138P, K152I, D160K or D160N, K162H, T164N, D165A, K173E, I182V, K190E, and K196S or K196T.

9. The intercellular labeling method of claim 1, wherein the sortase recognition sequence is LPXTG (SEQ ID NO: 1), in which X is any amino acid residue.

10. The intercellular labeling method of claim 1, wherein the sortase acceptor peptide is an oligoglycine.

11. The intercellular labeling method of claim 1, wherein the contacting step (iii) is performed in vitro.

12. The intercellular labeling method of claim 1, wherein the contacting step (iii) is performed in vivo.

13. The intercellular labeling method of claim 2, wherein the contacting step is performed in the presence of a candidate compound, and the method further comprises assessing whether the candidate compound modulates the interaction between the two members of the receptor-ligand pair, wherein a change of the labeling of the first cell in the presence of the candidate compound as compared with the labeling of the first cell in the absence of the candidate compound indicates that the compound is a modulator of the receptor-ligand pair.

14. The intercellular labeling method of claim 1, wherein the first cell is an antigen-presenting cell (APC) that expresses a MHC class I molecule, a MHC class II molecule, or both; and the second cell is a T cell that expresses a T cell receptor (TCR) molecule.

15. The intercellular labeling method of claim 14, wherein the APC is engineered to further express a polypeptide encoded by a member of a cDNA library.

16. The intercellular labeling method of claim 14, wherein step (i) is performed by providing a plurality of APCs which collectively express polypeptides encoded by a cDNA library; wherein step (iii) is performed by contacting the plurality of APCs with the T cell in the presence of the sortase substrate; and wherein the polypeptides encoded by the cDNA library are in addition to the first polypeptide that comprises the sortase acceptor peptide.

17. The intercellular labeling method of claim 16, further comprising isolating the labeled APCs produced in step (iii).

18. The intercellular labeling method of claim 4, wherein the first cell is a T cell, and the second cell is a B cell, or wherein the first cell is a B cell, and the second cell is a T cell.

19. The intercellular labeling method of claim 8, wherein the mutant sortase A contains mutations P94S, D160N, and K196T.

20. The intercellular labeling method of claim 9, wherein the sortase recognition sequence is LPETG (SEQ ID NO: 2).

21. The intercellular labeling method of claim 10, wherein the oligoglycine consists of 1-5 glycine residues.

22. The intercellular labeling method of claim 2, wherein the first polypeptide comprises CD40 and the N-terminal sortase acceptor peptide, which is oligoglycine GGGGG (SEQ ID NO: 3), and the second polypeptide comprises CD40L, which is fused to the sortase or the active fragment thereof.

23. The intercellular labeling method of claim 12, wherein the first cell, the second cell, or both are endogenous cells of a transgenic mouse, rat, or rabbit.

24. The intercellular labeling method of claim 12, wherein the first cell, the second cell, or both are constructed in vitro and transferred into a non-human subject.

25. The intercellular labeling method of claim 24, wherein the subject is a mouse, a rabbit, a rat, or a monkey.

26. The intercellular labeling method of claim 12, wherein the substrate comprising the sortase recognition sequence is administered to a non-human subject.

27. The intercellular labeling method of claim 12, wherein the contacting step is carried out in a germinal center.

28. The intercellular labeling method of claim 14, wherein the APC cell is a B cell, a dendritic cell, a macrophage, or a B cell.

29. The intercellular labeling method of claim 17, further comprising identifying the member of the cDNA library that is expressed in the labeled APCs.

30. The intercellular labeling method of claim 13, wherein a decrease of the labeling of the first cell in the presence of the candidate compound as compared to the level of labeling of the first cell in the absence of the candidate compound indicates that the compound inhibits the interaction between the ligand and receptor.

31. The intercellular labeling method of claim 13, wherein an increase of the labeling of the first cell in the presence of the candidate compound as compared to the level of labeling of the first cell in the absence of the candidate compound indicates that the compound enhances the interaction between the ligand and receptor.

* * * * *